United States Patent
Cros

(10) Patent No.: US 8,669,770 B2
(45) Date of Patent: Mar. 11, 2014

(54) SELECTIVELY ACTUATING WIRELESS, PASSIVE IMPLANTABLE SENSOR

(75) Inventor: Florent Cros, Decatur, GA (US)

(73) Assignee: CardioMEMS, Inc., Atlanta, GA (US)

( * ) Notice: Subject to any disclaimer, the term of this patent is extended or adjusted under 35 U.S.C. 154(b) by 638 days.

(21) Appl. No.: 12/946,407

(22) Filed: Nov. 15, 2010

(65) Prior Publication Data

US 2011/0115497 A1    May 19, 2011

Related U.S. Application Data

(60) Provisional application No. 61/261,609, filed on Nov. 16, 2009.

(51) Int. Cl.
    *G01R 35/00*    (2006.01)
(52) U.S. Cl.
    USPC ........................................................ 324/601
(58) Field of Classification Search
    USPC ............ 324/601, 633, 762.01–762.1; 702/75; 257/48; 438/14–18
    See application file for complete search history.

(56) References Cited

U.S. PATENT DOCUMENTS

| 5,680,106 | A | 10/1997 | Schrott et al. | |
|---|---|---|---|---|
| 5,796,334 | A | * | 8/1998 | Chen et al. ................. 340/539.3 |
| 6,165,135 | A | | 12/2000 | Neff |
| 7,262,677 | B2 | | 8/2007 | Kubota et al. |
| 7,936,174 | B2 | * | 5/2011 | Ellis et al. ..................... 324/654 |

OTHER PUBLICATIONS

International Search Report and Written Opinion for International Application No. PCT/US2010/056709 (mailed Jul. 28, 2011).

* cited by examiner

*Primary Examiner* — Tung X Nguyen
(74) *Attorney, Agent, or Firm* — Ballard Spahr LLP

(57) ABSTRACT

A wireless sensor having a primary passive electrical resonant circuit that has an intrinsic electrical property that is variable in response to a characteristic of a patient and a secondary passive electrical resonant circuit. In one aspect, the primary passive resonant circuit can be positioned into a tuned position in response to the actuation of the secondary passive electrical resonant circuit. In a further aspect, in the tuned position, the primary passive electrical resonant circuit, in response to an energizing signal produced by an ex-vivo source of RF energy, is configured to generate a sensor signal characterized by a resonant frequency that is indicative of the characteristic.

42 Claims, 18 Drawing Sheets

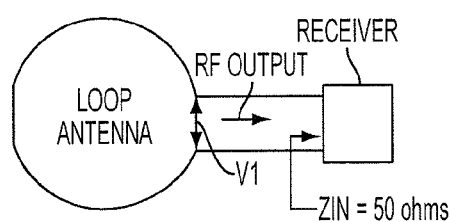
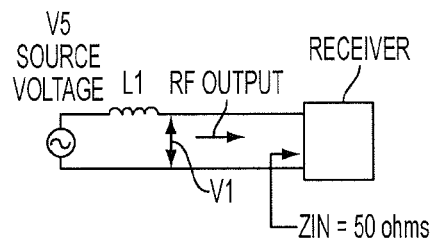
FIG. 16A     FIG. 16B
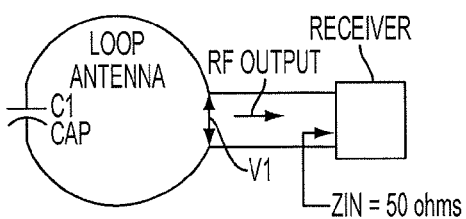
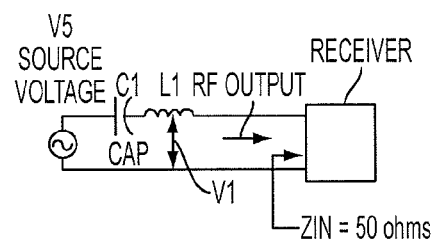
FIG. 17A     FIG. 17B
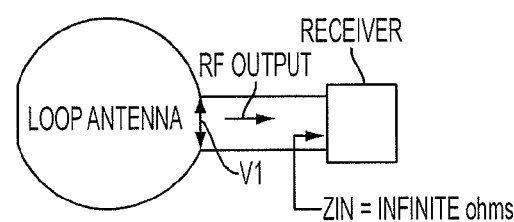
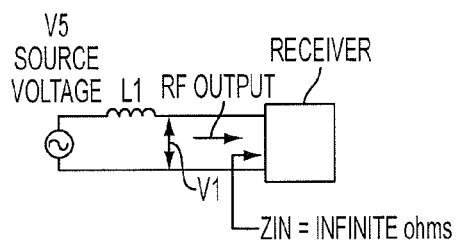
FIG. 18A     FIG. 18B

SELECTIVELY ACTUATING WIRELESS, PASSIVE IMPLANTABLE SENSOR

CROSS-REFERENCE TO RELATED APPLICATION

This application claims priority to and the benefit of U.S. Provisional Application No. 61/261,609, filed Nov. 16, 2009, which is incorporated in its entirety in this document by reference.

BACKGROUND OF THE INVENTION

1. Field of the Invention

The present invention generally relates to systems and apparatus for determining the state of multiple sensors within magnetic proximity to one another and are implanted within a living being, and more particularly, to sensors including switches that tune and detune a plurality of sensors selectively.

2. Background

The assignee of the present invention has developed and commercialized wireless pressure sensors utilizing an LC circuit encased in a hermetic housing. The resulting sensor exhibits a characteristic resonant frequency. An external interrogation unit monitors a single sensor at a time by monitoring the electrical characteristics of the LC circuit. Multiple sensors in a single host can be interrogated on the condition that they are sufficiently far away from one another, in relative distance or in relative resonant frequencies, such that the external electronics can detect and independently acquire the signal from the sensor of interest without any parasitic effects caused by other sensors. Yet, if the sensors are too close to each other, the signal is compromised and an accurate reading can be difficult to obtain.

It is desirable to be able to detect physical characteristics, e.g., pressure or temperature, via passive, wireless sensors at locations in close proximity. Thus, there is a need for a reliable and reversible way to selectively turn on and off wireless sensors while retaining the benefits of passivity.

SUMMARY

This application relates to passive, wireless sensors utilizing switches that can be turned on and off on demand and in a reversible and reliable manner. The present invention further comprises systems utilizing multiple sensors and the methods associated therewith.

Another aspect of the present invention includes a system of sensors implemented in medical interventional devices. Without limitation, the system of sensors can selectively comprise sensors such as pressure sensors, temperature sensors and the like. According to one example, a system to determine the rate of flow of blood across an artificial valve is contemplated. At least one sensor monitors pressure upstream of the valve, while at least one sensor measures pressure downstream from the valve. In this case, the sensors would be, e.g., mounted on opposing sides of the valve and in close proximity. The blood flow rate can be computed from the pressure data and other known values. Alternatively, it is contemplated that the switching sensors described herein can be used in other medical interventional devices such as, for example and without limitation, in shunts, ortho prostheses devices, and the like.

Yet another exemplary aspect, the system of sensors can comprise both a wireless pressure and temperature sensor. This exemplary system can comprises two LC (or LRC) circuits with two distinct resonant frequencies in range of the interrogator, one circuit being altered in response to local pressure and one to local temperature. The implementation of switching capability described herein allows for relatively close positioning of the resonant structures, which would be otherwise be problematic.

DETAILED DESCRIPTION OF THE FIGURES

FIG. 16A illustrates a exemplary coupling loop that is un-tuned and FIG. 16B illustrates its equivalent circuit.

FIG. 17A illustrates a loop that is tuned and FIG. 17B illustrates its equivalent circuit.

FIG. 18A illustrates a loop terminated into a receiver with a high input impedance and FIG. 18B illustrates its equivalent circuit.

Figure 20:
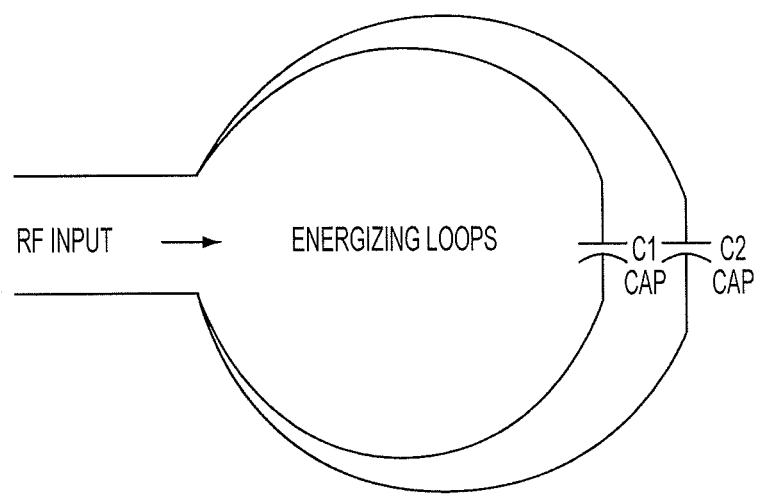

FIG. 20 schematically illustrated two stagger tuned loops.

Figure 21:
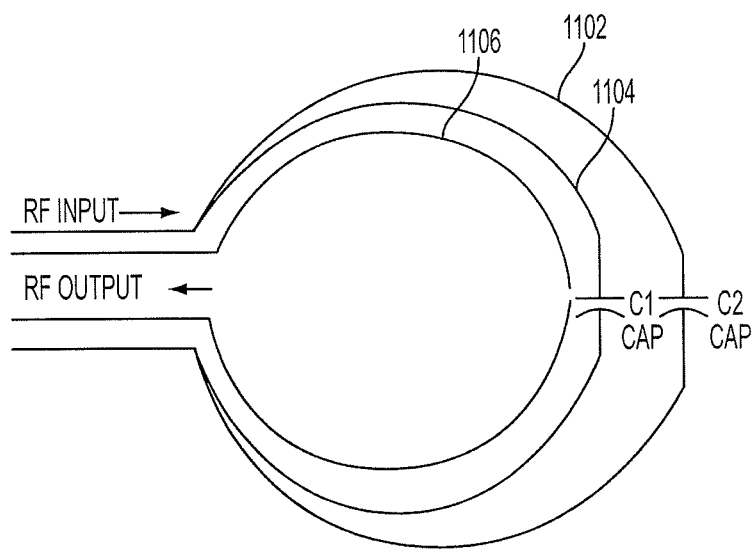

FIG. 21 illustrates the assembly of two stagger-tuned loops for transmitting the energizing signal to the passive electrical resonant circuit of the assembly and one un-tuned loop for receiving the output signal.

Figure 22A:
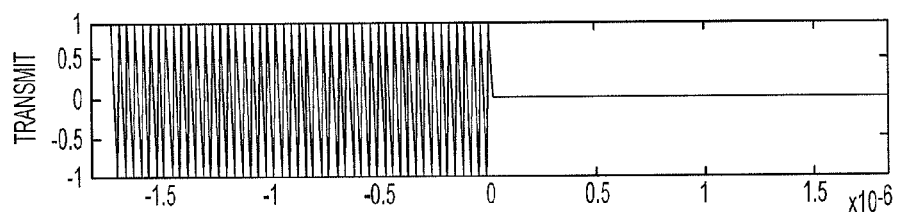

FIG. 22A is a graph illustrating an exemplary energizing signal.

Figure 22B:
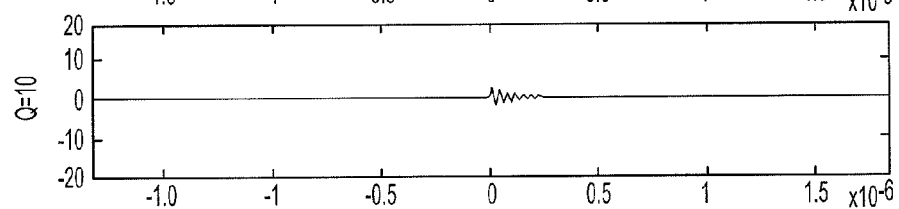
Figure 22C:
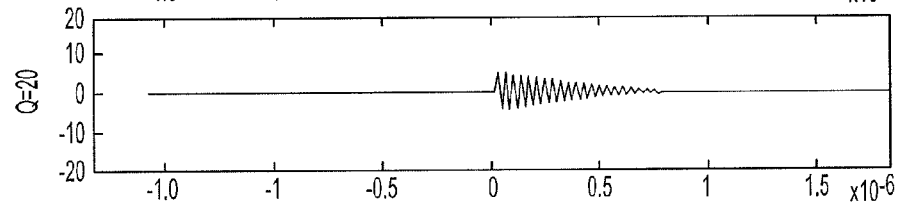
Figure 22D:
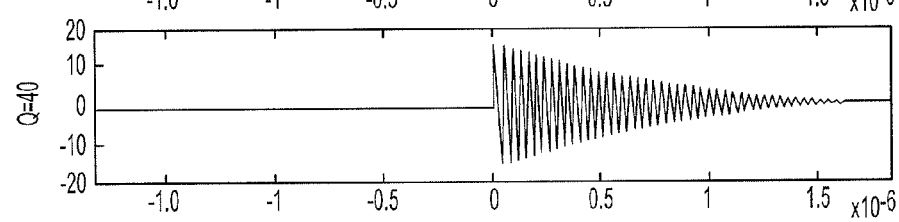

FIGS. 22B, 22C and 22D are graphs illustrating exemplary coupled signals.

Figure 23:
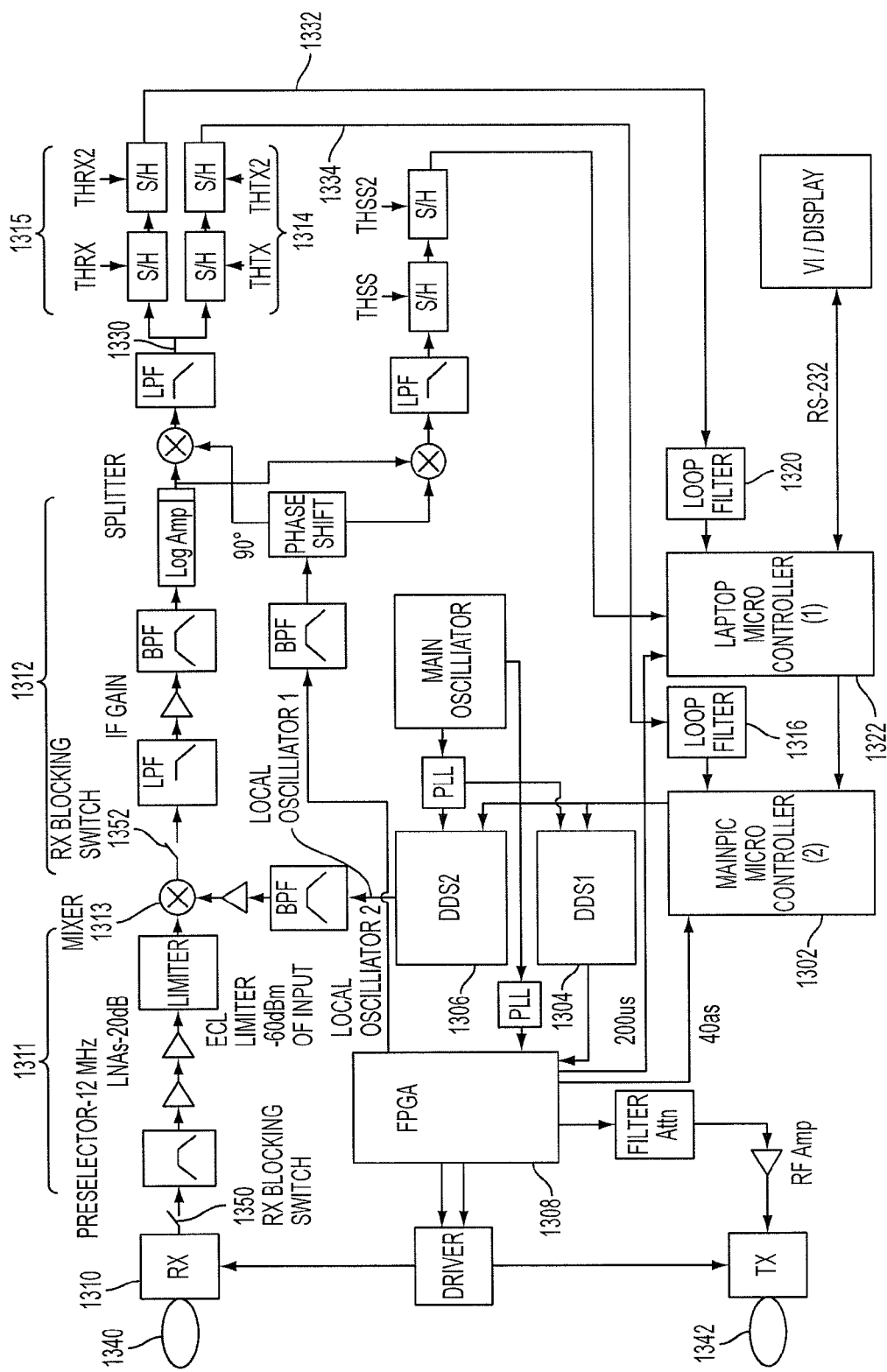

FIG. 23 is a schematic block diagram of an exemplary base unit of an interrogation system.

Figure 24A:
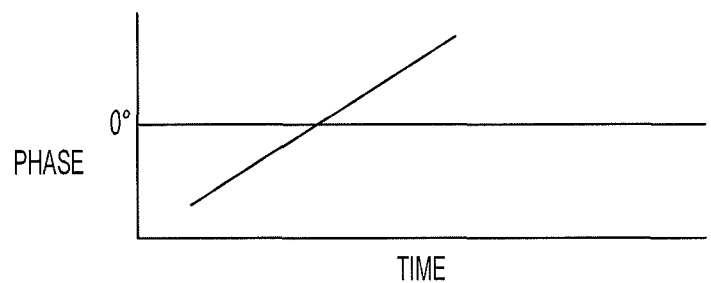
Figure 24B:
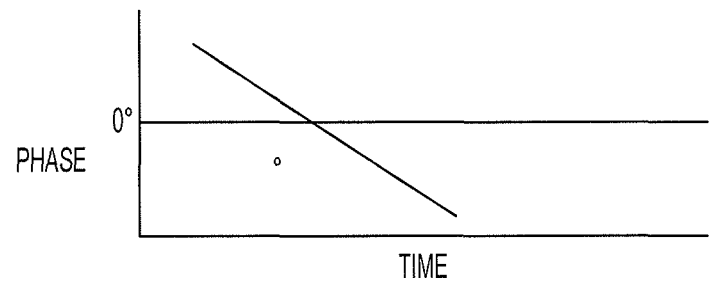

FIGS. 24A and 24B are graphs illustrating exemplary phase difference signals.

Figure 25:
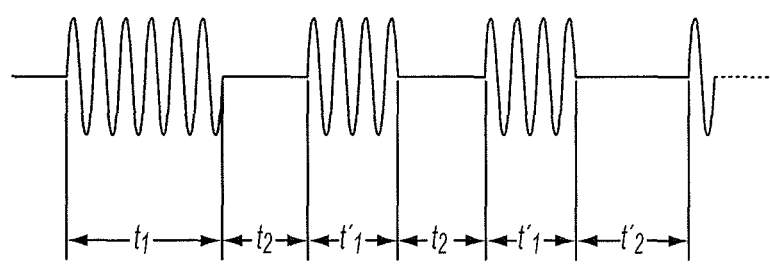

FIG. 25 illustrates frequency dithering.

Figure 26:
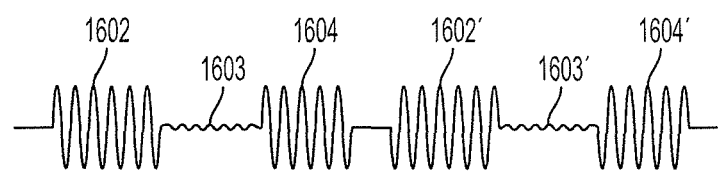

FIG. 26 illustrates phase dithering.

Figure 27:
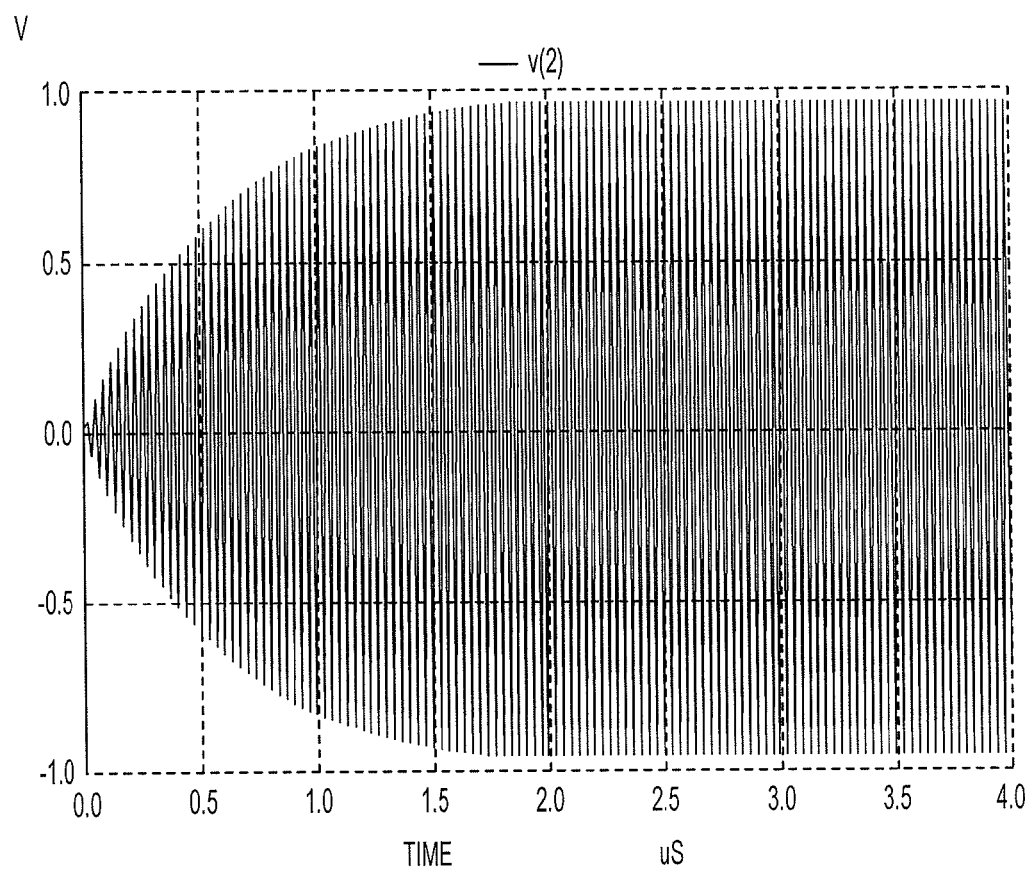

FIG. 27 is a graph illustrating an exemplary charging response of an LC circuit.

Figure 28:
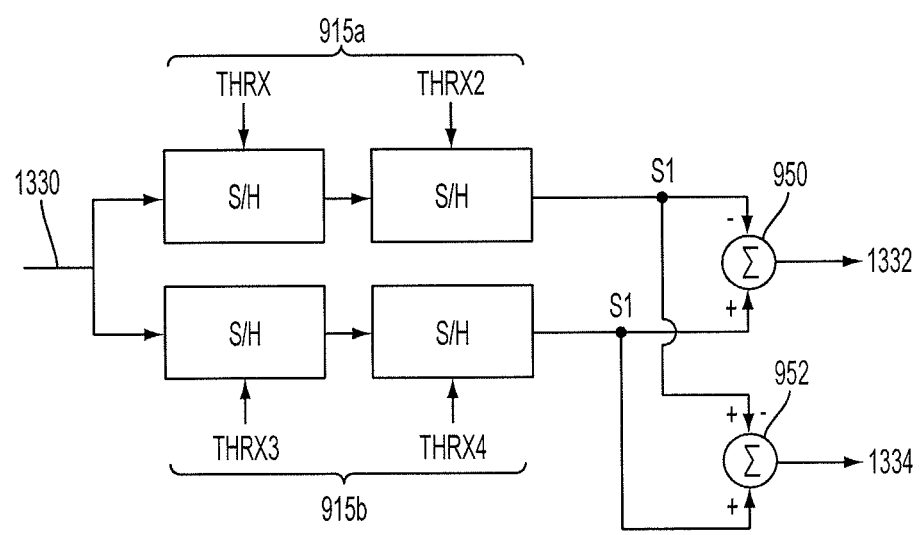

FIG. 28 is a partial schematic block diagram of a portion of an embodiment of an exemplary base unit of an interrogation system.

Figure 29:
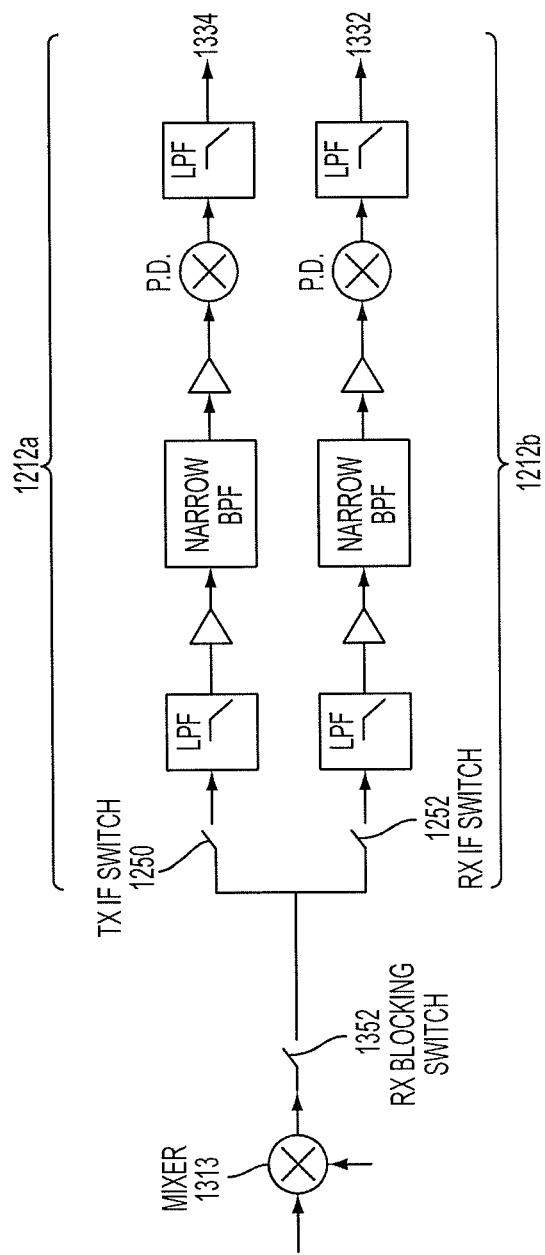

FIG. 29 is a partial schematic block diagram of a portion of an embodiment of an exemplary base unit of an interrogation system.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an assembly" can include two or more such assemblies unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

It is noteworthy that the resonant frequency (f) can not be destroyed unless the LC circuit is broken. Thus, as used throughout, the "on" and "off" states referred to in this document will refer respectively to "tuned" and "detuned" states of the sensor. Specifically, the terms "on" and "tuned" will refer to a sensor whose frequency is in range with the interrogator and the terms "off" and "detuned" will refer to a sensor whose frequency is out of range of the interrogator. Ideally, in the "off" state, the detuned frequency will be substantially out of range of any high or low pass filtering system associated with the interrogator.

Commonly assigned U.S. patent application Ser. Nos. 12/349,606, 12/175,803, 11/717,967, 11/613,645, 11/472,905, 11/276,571, 11/157,375, 11/105,294, and 10/943,772 are incorporated herein by reference in their entirety.

As used herein, a switch refers to a device for selectively coupling portions of the electrical LC circuit that comprises the sensor. Some examples of switches contemplated in the present invention include, but are not limited to, solid state metal-oxide-semiconductor field-effect-transistors (MOSFET) coupled with either an associated drive electronic or a magnetically-actuated mechanical device. These components are readily commercially available and can be selected with thermal, reliability, ease of interconnection considerations in mind.

Another aspect of this invention is a system that comprises a plurality of passive sensors that can be selectively turned on and off as well as an ex-vivo interrogator that can be configured to optionally affect at least one of selectively energizing at least one sensor, receiving a return or output signal from at least one sensor, processing the return signal, and displaying processed data derived from the at least one sensor.

Figure 1:
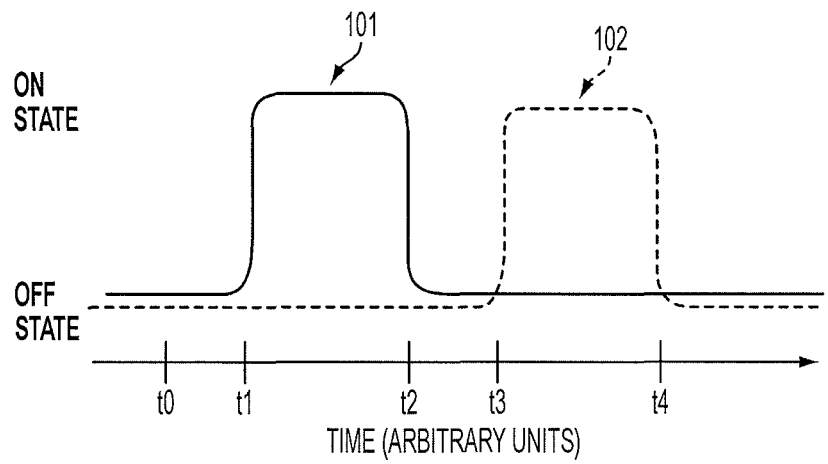
FIG. 1 illustrates an exemplary diagram of a circuit for configured to selectively switch between two sensors.

In one aspect, disclosed are passive, wireless sensors capable of being selectively turned on and off. One non-limiting example of "on" and "off" timing for two sensors is shown in FIG. 1. In this aspect, while a first sensor 101 is switched on, a second sensor 102 is switched off. T1, T2, T3 and T4 refer to specific, predetermined times. At T0, both the sensors 101, 102 are off. Between T1 and T2, the first sensor 101 is on while the second sensor 102 is off. From times T2 to T3, both the first sensor 101 and the second sensor 102 are off. Between times T3 to T4, the second sensor 102 is on and the first sensor 101 off. After T4, both sensors 101, 102 return to an off state. It is contemplated that the described "on/off" sequence can be repeated cyclically for as many cycles as desired to collect the relevant data. Many other switching schemes are possible and contemplated by the present invention, including the addition of more than two sensors, thus this illustration is not intended to be limiting. The characteristic intended to be illustrated here is that only one sensor is selectively "on" at a time; thus an interrogator will be able to acquire reliable data for all of the respective sensors, regardless of the respective spacing of the sensors relative to each other.

Conventionally, a passive (no battery) LC resonant circuit is composed of two electrical passive components that are connected in series: (a) a coil, or inductor ("L"), (b) a capacitor ("C"). Such a passive electrical circuit exhibits electrical resonance when subjected to an alternating electromagnetic field. The electrical resonance is particularly acute for a specific frequency value or range of the impinging signal. When the impinging signal substantially reaches the resonant frequency of the LC resonant circuit inside the sensor, a pronounced disturbance of the field can be detected wirelessly. In the simplest approximation, the electrical resonance occurs for a frequency f, related to the value of L and C according to Equation 1:

$$f = (2\pi(LC)^{1/2})^{-1} \qquad \text{(Equation 1)}$$

The passive electrical resonant circuit for the assemblies described herein that utilize a passive electrical resonant circuit can be fabricated via conventional MEMS approach to sensor design, which lends itself to the fabrication of small sensors that can be formed using, for example and without limitation, biocompatible polymers, ceramics and the like as substrate materials. In a further aspect, appropriately biocompatible coatings can be applied to the surfaces of the respective assemblies in order to prevent adhesion of biological substances to the respective assemblies that could interfere with their proper function.

In one example, the passive electrical resonant circuit of the assembly can be manufactured using Micro-machining techniques that were developed for the integrated circuit industry. An example of this type of sensor features an inductive-capacitive (LC) resonant circuit with a variable capacitor is described in Allen et al., U.S. Pat. No. 6,111,520, which is incorporated herein by reference. In this sensor, the capacitance varies with the pressure of the environment in which the capacitor is placed. Consequently, the resonant frequency of the exemplary LC circuit of the Allen pressure sensor varies depending on the pressure of the environment.

As described above, it is contemplated that the LC resonant circuit can comprise a coil inductor operably coupled to a capacitor. In various aspects, the inductance of the LC resonant circuit can be between about 0.1 to about 1000 micro-Henry, preferably between about 1 to about 100 micro-Henry, and more preferably between about 5 to about 15 micro-Henry. The capacitance of the LC resonant circuit can be between about 0.1 to about 1000 pF, preferably between about 0.5 to about 100 pF, and more preferably between about 1 to about 20 pF. The resonant frequency of the LC resonant circuit can be between about 0.1 to about 450 MHz, preferably between about 1 to about 60 MHz, and more preferably between about 25 to about 45 MHz. In addition, the quality factor at self resonance and the frequency range of the self-resonant frequency itself can be between about 5 to 120, preferably between about 5 to about 80, and more preferably between about 10 to about 70.

In one aspect, the coil inductor of the LC resonant circuit can be a substantially planar spiral inductor. Optionally, the coil inductor of the LC resonant circuit can have a longitudinal axis and the respective windings of the coil inductor can spiral about and extend along the longitudinal axis. In this aspect, at least a portion of each winding of the coil is non-planer with respect to the longitudinal axis. For example, in a representative cross-sectional plane that is substantially transverse to the longitudinal axis, portions of the windings in the y-axis can be below the cross-sectional plane and portions of the winding in the y-axis can be above the cross-sectional plane.

In one aspect, the inductor coil can be comprised of the inductor coil body and the coil leads. One skilled in the art will appreciate that numerous parameters of the inductor coil can be varied to optimize the balance of size and the electrical properties of the circuit, including the materials, coil diameter, wire gage, number of coil windings, and cross-sectional area of the coil body. Typically, the material of the coil must be highly conductive and also biocompatible. Suitable materials include, but are not limited to, gold, copper and alloys thereof. If the wire is sufficiently strong, the coil can be self-supporting, also known as an "air core" configuration. A solenoid coil is another suitable configuration. If the wire is not sufficiently strong to be unsupported to maintain its intended configuration during assembly and in use, the coil can be formed around a central bobbin comprised of a suitable dielectric material. In the alternative, the wound coil can be encased in a liquid polymer that can cure or otherwise harden after it is applied to the coil body. Polyimide is one preferred material for this application because of its thermal, electrical, and mechanical properties. However, processes achieving substantially similar results that involve lower processing temperatures would make other polymer choices desirable, such choices being obvious to one skilled in the art.

Optionally, it is contemplated that the passive electrical circuit of the sensor can be housed within a substantially non-permeable enclosure or housing to ensure the protection of the passive electrical circuit of the sensor when the respective sensor is positioned within the living being. In this aspect, the passive electrical circuit of the sensor can be protected from deleterious agents such as corrosion, parasitic excessive strain/stress, biological response, etc. . . . As one will appreciate, it is contemplated that the enclosure can be formed of materials that substantially prevent any undesired fluids and/or gases from passing or diffusing through the walls of the enclosure, utilizing manufacturing processes that eliminate undesired holes that could otherwise permit such passing of undesired fluids or gases.

In another aspect, the enclosure can be formed of materials that do not allow any undesired fluids and/or gases from passing or diffusing through the walls of the enclosure. Exemplary enclosure material can include, without limitation, biocompatible polymer (such as, for example and without limitation, PEAK, PE, PTFE, FEP, semi-crystalline thermoplastic polymers, and the like), glass, fused-silica, low temperature glass, ceramics, quartz, pyrex, sapphire, sintered zirconia and the like. Optionally, the level of permeability can be a rate of fluid ingress or egress that changes the original capacitance of the LC circuit by an amount preferably less than 10 percent, more preferably less than 5 percent, and most preferably less than 1 percent over the accumulated time over which measurements will be taken.

Optionally, it is also contemplated that the housing can define an internal cavity in which at least a portion of the passive electrical circuitry can be disposed. In a further aspect, a known and invariant quantity of gas can be added to the internal cavity of the housing. In another aspect, it is contemplated that the enclosure can be formed of materials that will not allow the resonant circuit of the pressure sensor to flex in response to relative motion of the implant that the sensor is mounted thereon or other forces that can be otherwise applied to the sensor. In yet another aspect, the passive circuits comprising a first sensor and additional sensors can be housed in a single enclosure.

Q factor (Q) is the ratio of energy stored versus energy dissipated. The reason Q is important is that the ring down rate of the sensor is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, in one aspect, the sensor can be configured with values of Q sufficiently high enough to avoid unnecessary increases in complexity in communicating with the at least one pressure sensor via external electronics. In one aspect, the Q of the sensor can be dependent on multiple factors such as, for example and without limitation, the shape, size, diameter, number of turns, spacing between the turns and cross-sectional area of the inductor component. In addition, Q will be affected by the materials used to construct the pressure sensor. In one example, the sensor can be formed from materials with low loss tangents to effect a sensor with higher Q factors.

In another aspect, the exemplary enclosure materials help to provide the desired biocompatibility, non-permeability and/or manufacturing processing capabilities of the sensor containing the resonant circuit. These exemplary materials are considered dielectrics, that is, they are poor conductors of electricity but are efficient supporters of electrostatic or electroquasistatic fields. A dielectric material has the ability to support such fields while dissipating minimal energy. In this aspect, the lower the dielectric loss, the lower the proportion of energy lost, and the more effective the dielectric material is in maintaining high Q.

With regard to operation within the human body, there is a second issue related to Q, namely that blood and body fluids are conductive mediums and are thus particularly lossy. As a consequence, when a sensor having a resonant circuit is immersed in a conductive fluid, energy from the sensor will dissipate, substantially lowering the Q and reducing the pressure sensor-to-electronics distance. In one aspect, the loss can be minimized by further separation of the sensor having the resonant circuit from the conductive liquid, which can be accomplished, for example and without limitation, by coating at least a portion of the sensor having the resonant circuit in a suitable low-loss-tangent dielectric material.

Figure 2:
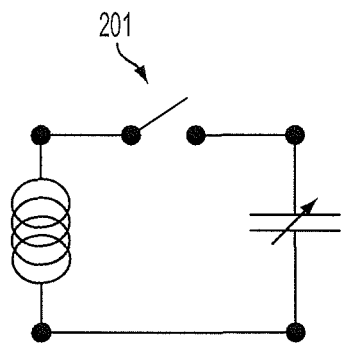
FIGS. 2-4 illustrate exemplary schematic embodiments of resonant circuits that are configured with a selective switching capability.
Figure 3:
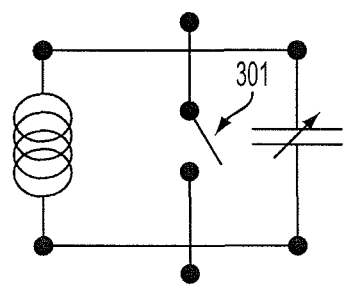
Figure 4:
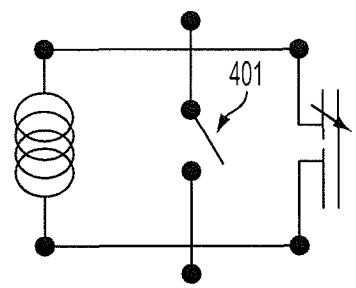

Referring now to FIGS. 2-4, exemplary, non-limiting, configurations of resonant circuits that are functionalized with a selective switching capability are shown. In one aspect, FIG. 2 shows a switch 201 implemented in series with a sensitive (i.e., variable) capacitor 202 and a fixed inductor. 203 In another aspect, FIG. 3 shows a switch 301 implemented in parallel relative to the sensitive capacitor 302 and fixed inductor 303 of the circuit. Finally, FIG. 4 shows a switch 401 implemented in parallel with a sensitive split plate capacitor 402 and a fixed inductor 403 of the circuit. It is contemplated that these exemplary circuit diagrams illustrate possible switching modalities relative to the basic resonant circuit components and do not preclude the addition of subsequent elements to the circuit or alteration of the depicted elements in the exemplary circuits. Accordingly, both the L and C can be fixed and an additional circuit elements may be included such as, but not limited to, resistors or diodes. Also, the C can be fixed and the L could be variable. Further, both the L and C can be fixed and a material whose dielectric constant changes with the sensed parameter can be employed.

In another aspect, the switch can be configured to minimize adverse functionality of the sensor. It is preferred that the switch be configured to not impede the function or performance of the sensor. In one non-limiting example, the switch can be configured to avoid being a source of additional parasitic capacitance on the circuit as this can dampen the overall sensitivity of a LC based sensor based on variable capacitance. Similarly, the switch can be configured to minimize or prevent leakage of currents that are significant enough to reduce the Q factor of the resonant circuit to a degree that would impair detection of the sensor by the interrogator.

In one aspect, the "on-off" switch of the present invention can be actuated wirelessly. In this aspect, the energy required to actuate the switch can be, e.g., provided by the external interrogation system. Also, the switch should not impede the function or performance of the sensor.

Figure 5:
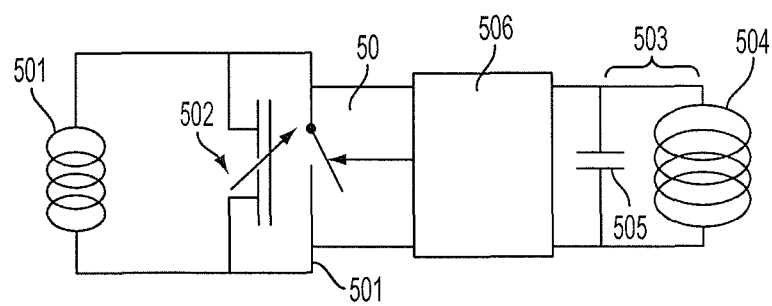
FIG. 5 illustrates a schematic embodiment of a resonant circuit that is configured with a selective switching capability and shows an RF actuated switch implemented in a LC Sensor.

In one embodiment, and as shown in FIG. 5, an RF actuated switch implemented in a LC sensor is shown. The sensor circuit comprises a primary LC circuit, an inductor 501 and sensitive capacitor 502. An on-off switch 500 is electrically coupled across the inductor 501. A secondary LC resonant circuit comprising an inductor 504 and a capacitor 505, is configured to resonate at a predetermined fixed frequency, fswitch. In this sensor circuit, the secondary resonant circuit harvests energy received from the ex-vivo interrogator (not shown), at the frequency (fswitch) of the transmitted RF energy. In one aspect, it is contemplated that the received energy can be a burst of electromagnetic energy that is outside the resonant frequency of the sensitive, primary resonant circuit, but, in one aspect, can be within the Q bandwidth of the sensor to get good distance during acquisition. In another aspect, the energy stored by the second resonant circuit 503 can is rectified, stored and selectively dispensed by a ASIC circuit 506 to actuate switch 500.

Figure 6:
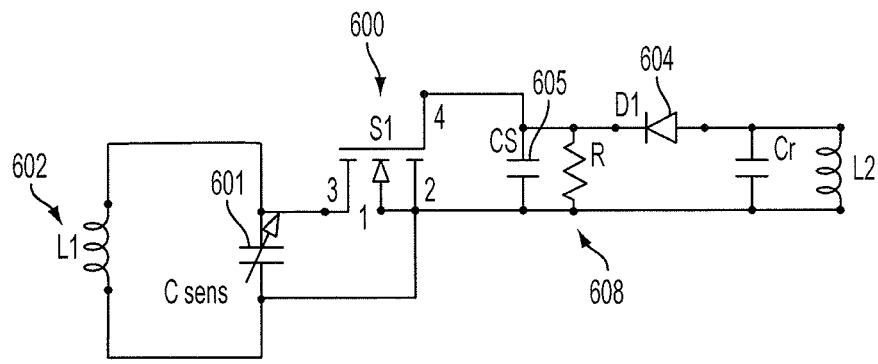
FIG. 6 illustrates a schematic embodiment of a resonant circuit that is configured with a selective switching capability and shows an RF switching configuration that uses an N-type MOSFET switch.

FIG. 6 represents an RF switching scheme using N-type MOSFET (Metal Oxide Semiconductor Field Effect Transistor) switch. In this aspect, the exemplary N-type MOSFET-based switching configuration can be configured such that the default state of the sensor is on and the temporary switched position is off. In this aspect, the N-type MOSFET switch is configured to turn off a sensor for a select predetermined amount of time. As one skilled in the art will appreciate, in this exemplified circuit, the sensing capacitor 601 is shorted out by switch 600 as long as the gate of the switch 600 is powered. As illustrated, the LC circuit is shown temporarily turned off. In one aspect, to turn the sensor off, a specific "disabling" signal can be broadcasted by the external interrogator. In one example, this signal can be a monochromatic RF EM wave having a frequency fswitch that can be chosen to accommodate FCC or country frequency regulations and is outside the frequency range of the sensing LC circuit 601, 602. In one aspect, higher frequencies, e.g., at or near 400 MHz, are potentially useful as well for reasons pertaining to the physical size of the secondary LC circuit 610, which is comprised of inductor 614 and capacitor 612. In one aspect, by using multiple sensors with different resistive values at resistor 608, multiple sensors can be turned off simultaneously with a single signal and can be returned to an "on" state in a predetermined sequence. This enables the interrogator to sequentially sense multiple resonant circuits in close proximity to each other.

Figure 7:
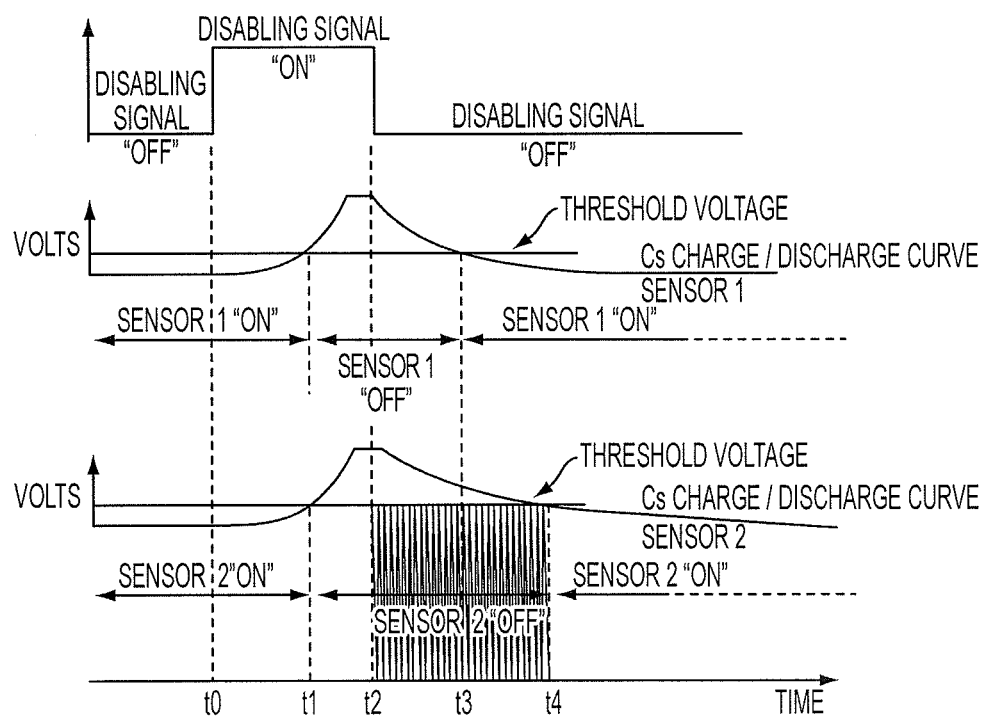
FIG. 7 is a graphical illustration of a timing sequence for the schematic of FIG. 6.

FIG. 7 is a graphical representation of a timing sequence using the sensor schematic of FIG. 6. The resting state of the sensor circuit is on, as indicated from time 0 to T1. The monochromatic RF EM signal that is harvested by the secondary resonant circuit 610 is rectified through a first diode 604 and accumulates at capacitor 605. When a sufficient charge is built up, capacitor 605 turns on an N-MOSFET low-power switch 600 which, in turn, shorts out the sensing capacitor 601 and detunes the sensing LC circuit 601, 602. One skilled in the art will appreciate that the resonant circuit will remain off while capacitor 605 discharges through resistor 608 so long as the voltage across the capacitor remains higher than a predetermined threshold value, imposed in part by the N-MOSFET switch.

In FIG. 7, the "off" time is selected to be from T1 to T3 for a first sensor and from T1 to T4 for a second, separate sensor. A resistor 608, together with capacitor 605, determines the respective time that the sensing LC circuit 601, 602 is shorted out. This is known as the RC time constant and can be configured to be from a few microsecond to a few minutes depending on the characteristics of the resistor and capacitor that are used. For example, and without limitation, the RC time constant can be between about 1 microseconds to about 500 microseconds, preferable between about 5 microseconds to about 250 microseconds, and more preferably about 10 microseconds to about 100 microseconds.

As one will appreciate, when the value of resistor 608 is large, the sensor stays longer in the "off" state. Optionally, leakage current in capacitor 605, diode 604 and switch 606 will govern the disabling time without resistor 608. As one will appreciate, this exemplified mode of operation does not require the disabling signal to be broadcast continuously. Thus, it is contemplated that the ex-vivo interrogator can detect LC resonance system of the first sensor from T3 to T4 and the second sensor from T4 and later, without interference between the respective first and second sensors.

Figure 8:
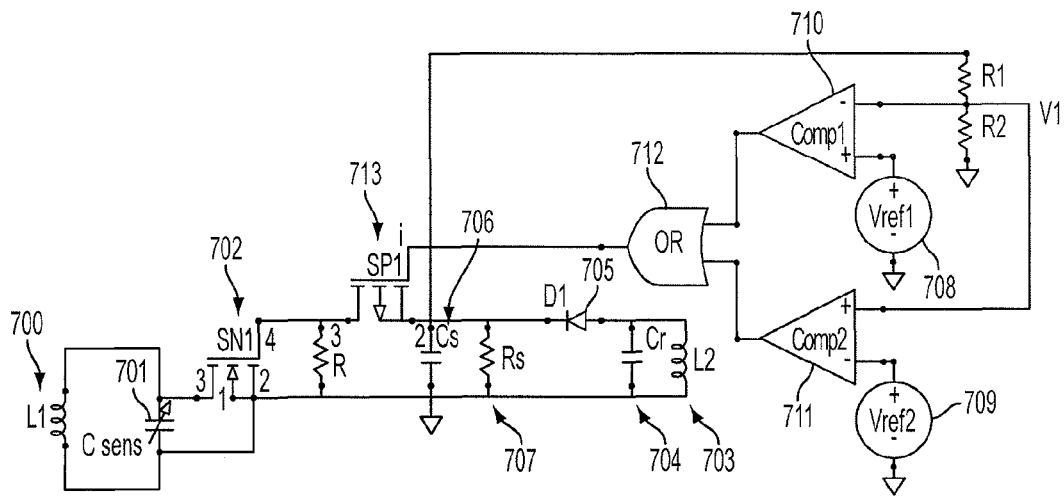
FIG. 8 illustrates a schematic embodiment of a sensor circuit in which the resting state of the sensor circuit is "off" and the temporary energized state is "on."

Referring now to FIG. 8, an exemplary sensor circuit schematic is illustrated in which the resting state of the sensor circuit is "off" and the temporary energized state is "on." This configuration results in only one sensor resonating within a predetermined frequency range for any given time. In one aspect, the resonant circuit can be comprised of an inductor 700 and capacitor 701. Here the capacitor 701 can be electrically shorted out by switch 702, which can operatively turn off the resonant circuit during a predetermined time frame. In this aspect, in order to actuate switch 702, a RF EM signal at a predetermined monochromatic frequency can be broadcast from an external source.

In a further aspect of the sensor circuit shown in FIG. 8, a secondary resonant circuit comprised of a fixed inductor 703 and a fixed capacitor 704 can harvest energy from the broadcast RF EM signal. In another aspect, the resonance of the secondary resonant circuit can serve to boost the signal power. Subsequently, diode 705 rectifies the signal and capacitor 706 stores the energy. The DC voltage accumulates at capacitor 706 and is electrically coupled to switch 713. The voltage of capacitor 706 decays with a RC time constant defined by itself and resistor 707 and that can be set during manufacturing to be anywhere from a few microseconds to a few minutes depending on the characteristics of the resistor and capacitor used. For example, and without limitation, the RC time constant can be between about 1 microseconds to about 500 microseconds, preferable between about 5 microseconds to about 250 microseconds, and more preferably about 10 microseconds to about 100 microseconds.

The voltage stored at capacitor 706 can be applied across resistor 707 and V1 is derived with the relationship: R2/(R1+R2). Then, V1 will be compared to Vref1 708 and Vref2 709. Vref1 and Vref2 are derived from the voltage across capacitor 706 through low power voltage reference circuits. The output of comparators 710 and 711 are fed into the OR gate 712 and the output of OR gate 712 is applied to switch 713, that can, for example and without limitation, be a P-Type MOSFET switch. When the output of OR gate is high, the switch 713 is off, which prevents voltages from being electrically coupled to the detuning switch 702, which results the LC sensor being positioned in a default "on" position.

Figure 9:
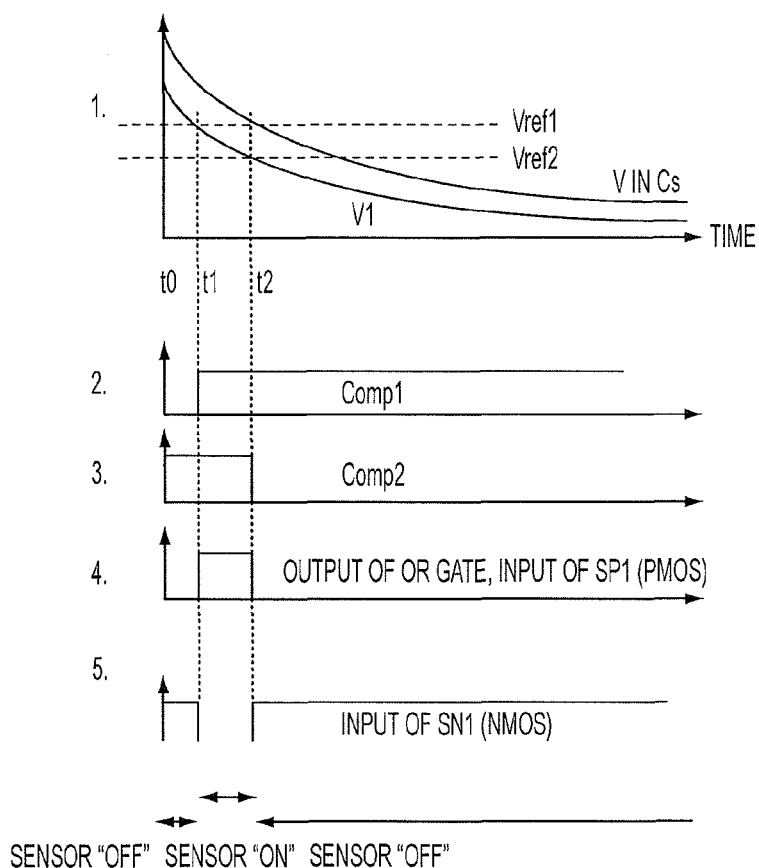
FIG. 9 is a schematic illustration of an exemplary sequence of events that occur after the sensor circuit of FIG. 8 is energized with a RF signal.

FIG. 9 is a diagram illustrating the sequence of events taking place once the sensor circuit illustrated in FIG. 8 is energized with the monochromatic RF EM signal. Between T0 and T1, V1 is higher than Vref1 708 and the output of comparator 710 is low. After T1, V1 is lower than Vref1 708 and the output of comparator 710 becomes high. After T2, V1 is lower than Vref2 709 and the output of comparator 711 becomes low. Thus, as exemplified, the OR gate 712 is high only during time between T1 to T2, which resulting in a window of time where the resonant circuit 700, 701 of the sensor circuit is "on."

In another aspect, MOSFET switches can comprise, without limitation, silicon and GaAs MOSFETs. Optionally, use of both depletion-mode and enhancement-mode MOSFETs are contemplated. Also contemplated for use in the present invention are other conventional types of switches such as, without limitation, bipolar transistors (e.g., an insulated gate bipolar transistor), which may offer some advantages such as higher trans-conductance, higher input impedance and overall lower trans-capacitance. On skilled in the art will appreciate that the selection of a switch will depend on the details of the particular integration approach.

It is contemplated that a plurality of sensors can be energized simultaneously with a single RF signal but turned on at distinct times afterwards by using sensors that have different respective ratios of R2/(R1+R2). In this aspect, a single interrogator can receive information from several sensors in relative proximity to each other with sequential order.

Figure 10:
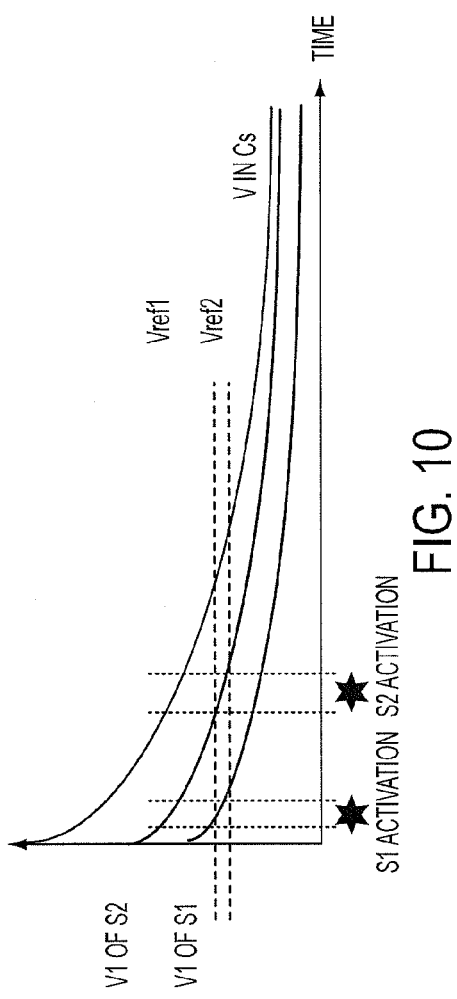
FIG. 10 is a graphical illustration of a timing sequence for the schematic of FIG. 8.

FIG. 10 illustrates exemplary timing of two sensors that each have the sensor circuit illustrated in FIG. 8. As one will appreciate and as contemplated, the differential timing activation can be achieved with many variations of the sensing schemes described above. In one aspect, one variation is to use resistors with different resistive values for each respective sensor.

Figure 11:
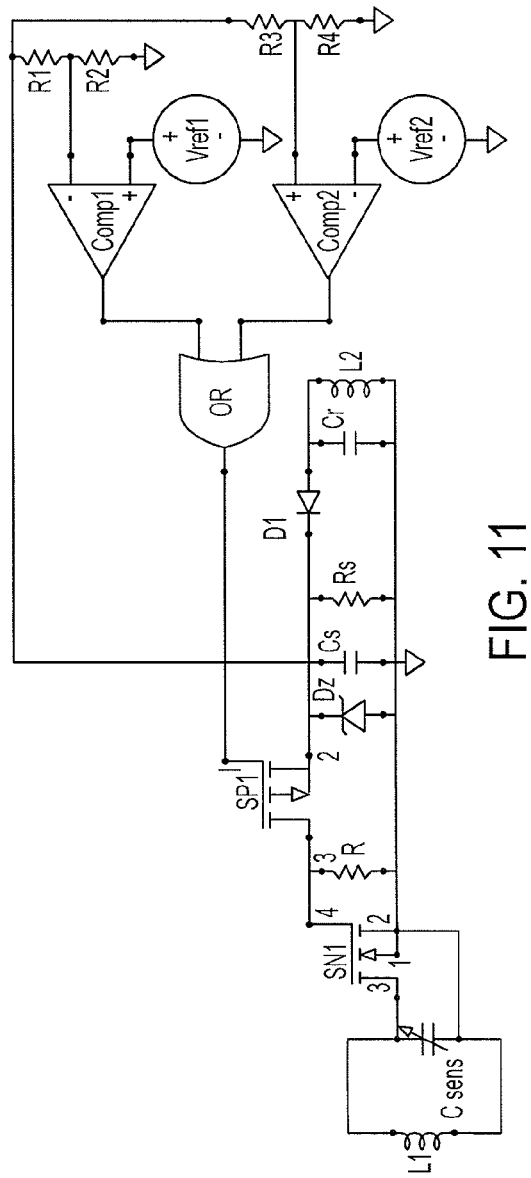
FIG. 11 illustrates a schematic embodiment of a sensor circuit that is configured to allow for timing control.

In another embodiment, FIG. 11 illustrates an exemplary sensor schematic of a sensor circuit that is configured to allow for timing control. In this aspect, a Zener diode (Dz) is added to each sensor circuit to increase the temporal stability of the sensor circuit. In this aspect, optionally there are four components which can govern the timing of the circuit, i.e., Vref1, Vref2, (R1+R2) and (R3+R4). In one aspect, a plurality or combination of the components can be used to affect the timing control. It is contemplated, in one exemplary aspect, any three of the four components can be used to affect the desired timing control. In one aspect, an exemplary dual "LC" sensor with a magnetically actuated toggling switch can comprise at least one inductor, at least two capacitors and at least one magnetically actuated toggle switch.

Figure 12:
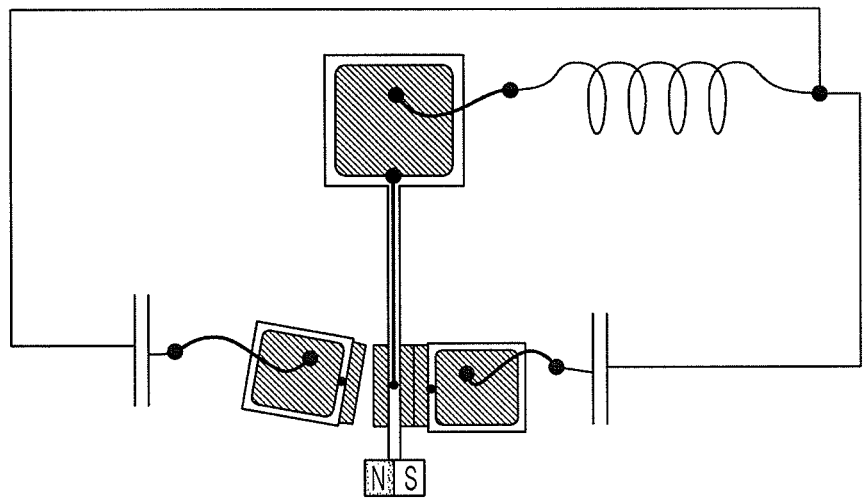
FIGS. 12 and 13 are schematic illustrations of a sensor circuit that is configured to selectively actuate LC circuits.
Figure 13:
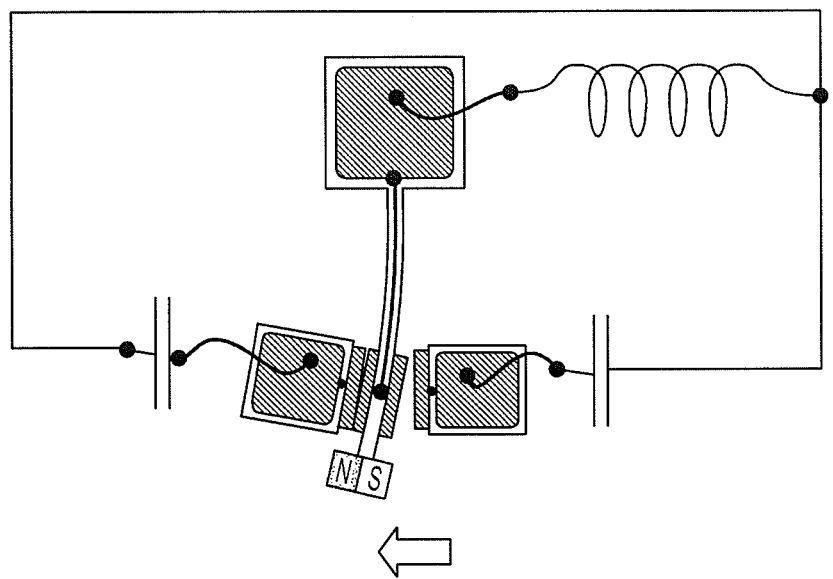

In a further embodiment and referring to FIGS. 12 and 13, one exemplary circuit configuration can comprises two capacitors C1 and C2, one inductor L and one switch S. In one aspect, one terminal of the inductor can be electrically coupled to one terminal of capacitor C1 and C2 to create an electrical trifurcation. In a further aspect, the switch S, when in its resting state (State 1) can be configured to electrically connect to the second terminal of the inductor L and to the second terminal of one of capacitors C1. In one example, and not meant to be limiting, the capacitor C1 can be designed to react predominantly to a specific environmental parameter change, such as, but not limited to, temperature. The resonant frequency of the resulting LC1 circuit, which can be interrogated remotely using interrogation devices and methods described herein, changes in function of the capacitance. Thus, in the example describe above, in which the specific environmental change is temperature, the resonant frequency of the resulting LC1 circuit reflects the value of the temperature surrounding the capacitor.

In the illustrated embodiment, by applying a desired external magnetic field, the switch can be temporarily toggled and thereby moved to assume a geometrical state that is substantially different than the geometry observed at the resting state. In this aspect, the desired external magnetic field can be a magnetic field that is sufficiently strong or substantially well aligned with respect to the switch S to result in the generation of local mechanical forces sufficiently strong to induce the switch to assume a geometrical state substantially different that the one assumed under the imposition of no or suboptimal external magnetic field.

In another aspect, when the switch is forced to assume a temporality toggled state, e.g., an actuated state, State 2, the second terminal of the inductor is temporarily disconnected from the second terminal of the capacitor C1 and temporarily connected to the second terminal of the capacitor C2. In one instance, the capacitor C2 can be designed to react predominantly to a specific environmental parameter change, such as but not limited to, environmental pressure. The resonant frequency of the LC2 circuit, interrogated remotely using the appropriate electronic apparatus, changes in function of the capacitance C2 and, in one example, reflects the value of the pressure surrounding the capacitor.

In one aspect, the fabrication of a two state toggle switch can be achieved using MEMS manufacturing methods. For example, in one aspect, a suitable magnetic switch can comprise an adequately sized flexible or deformable cantilever beam made entirely or at least partially of magnetic material, such as, for example and without limitation, electroplated Ni—Fe, permanent magnet, and the like. In one aspect, the cantilever beam geometry can be configured to preferentially bend substantially in a plane parallel to the substrate, instead of along a path that is substantially orthogonal to the substrate. In another aspect, the cantilever beam can be affixed at one end to the substrate, which can be formed from, for example and without limitation, glass, Silicium, metal, ferrite, and the like. In one aspect, a permanent magnet can be mounted to the free end of the beam.

In a further aspect, two sets of electrical contacts, which can each comprise a first and second electrical pads, can be positioned to flank portions of the opposing sides of the beam. In this aspect, a first electrical pad can be fixed to a portion of one side of the beam such that the first electrical pad can selectively engage, or stands in vis-à-vis with, a second electrical pad that is fixed to the substrate. In another aspect and for the opposed side of the beam, a first electrical pad can be fixed to a portion of the opposed side of the beam such that the first electrical pad can selectively engage, or stands in vis-à-vis with, a second electrical pad that is fixed to the substrate. In a further aspect, both of the first electrical pads fixed to the beam can be electrically coupled to a separate electrical pad that is coupled to one end of the inductor. In this aspect, the second electrical pads can be coupled to one terminal of either capacitor. Thus, under no external magnetic field, the beam assumes a geometry that results in pressing one electrical pad against its vis-à-vis of the first set of electrical contacts, thereby substantially establishing an electrical contact and resulting in connecting electrically one terminal of the inductor to one terminal of the first capacitor. It is contemplated that, under desired external magnetic field conditions, a force arises from the interaction of the magnetic field and the magnet affixed to the beam and, as long as the force is strong enough to overcome the flexural rigidity of the beam, the beam can be forced to assume a geometry that results in pressing the electrical pads forming the second set of electrical contacts together, thereby substantially establishing an electrical contact and resulting in connecting electrically one terminal of the inductor to one terminal of the second capacitor.

In another aspect, the system can be configured to provide a monochromatic blast of EM energy and to determine the resonant frequency and bandwidth using an impedance approach. In this approach, an initial frequency that is outside the frequency range of the sensing LC circuit is selected in order to energize the sensor. Then, an excitation signal is transmitted using a transmitting antenna to electromagnetically couple the passive sensing LC circuit to the transmitting antenna, which results in the modification of the impedance of the transmitting antenna. The measured change in impedance of the transmitting antenna allows for the determination of the resonant frequency and bandwidth of the passive sensing LC circuit. As the respective sensors are activated and deactivated during the duration of the excitation signal as exemplarily described above, the impedance of the transmitting antenna, coupled with the known RC time constants of the respective sensors provides a means to determine the resonant frequency and bandwidth of each individual sensor.

In another aspect, the system described herein provides for a system capable of determining the resonant frequency and bandwidth of the sensor using an impedance approach. In this approach, an excitation signal can be transmitted using a transmitting antenna to electromagnetically couple a sensor having a passive electrical resonant circuit to the transmitting antenna, which resultantly modifies the impedance of the transmitting antenna. The measured change in impedance of the transmitting antenna allows for the determination of the resonant frequency and bandwidth of the passive electrical resonant circuit of the sensor.

In a further aspect, the system described herein provides for a transmit and receive interrogation system configured to determine the resonant frequency and bandwidth of a resonant circuit within a particular sensor. In this exemplary process, an excitation signal of white noise or predetermined multiple frequencies can be transmitted from a transmitting antenna and the passive electrical resonant circuit of the sensor is electromagnetically coupled to the transmitting antenna. A current is induced in the passive electrical resonant circuit of the sensor as it absorbs energy from the transmitted excitation signal, which results in the oscillation of the passive electrical circuit at its resonant frequency. A receiving antenna, which can also be electromagnetically coupled to the transmitting antenna, receives the excitation signal minus the energy which was absorbed by the sensor. Thus, the power of the received or output signal experiences a dip or notch at the resonant frequency of the sensor. The resonant frequency and bandwidth can be determined from this notch in the power.

In one aspect, the transmit and receive methodology of determining the resonant frequency and bandwidth of a passive electrical resonant circuit of an sensor can include transmitting a frequency signal, such as, without limitation, a multiple frequency signal or a swept frequency signal, from a transmitting antenna to electromagnetically couple the passive electrical resonant circuit on the sensor to the transmitting antenna in order to induce a current in the passive electrical resonant circuit of the sensor. A modified transmitted signal due to the induction of current in the passive electrical circuit is received and processed to determine the resonant frequency and bandwidth.

In another aspect, the system can determine the resonant frequency and bandwidth of a passive electrical resonant circuit within a particular switched "on" sensor by using a chirp interrogation system, which provides for a transmitting antenna that is electromagnetically coupled to the resonant circuit of the sensor. In this aspect, an excitation signal of white noise or predetermined multiple frequencies can be applied to the transmitting antenna for a predetermined period of time to induce a current in the passive electrical resonant circuit of the sensor at the resonant frequency. The system then listens or otherwise receives an output signal that radiates from the energized passive electrical resonant circuit of the sensor. In this aspect, the resonant frequency and bandwidth of the passive electrical resonant circuit can be determined from the output signal.

In this aspect, the chirp interrogation method can include transmitting a multi-frequency signal pulse from a transmitting antenna; electromagnetically coupling a passive electrical resonant circuit on a switched "on" sensor to the transmitting antenna to induce a current in the resonant circuit; listening for and receiving an output signal radiated from the energized passive electrical signal of the sensor; determining the resonant frequency and bandwidth from the output signal, and resultantly, determining the measured characteristic acting on the respective sensor from the determined resonant frequency and bandwidth.

In a further aspect, the system described herein can provide an analog system and method for determining the resonant frequency of a passive electrical resonant circuit within a particular sensor. The analog system can comprise a transmitting antenna coupled as part of a tank circuit, which, in turn, is coupled to an oscillator. In this aspect, a signal is generated which oscillates at a frequency determined by the electrical characteristics of the tank circuit. The frequency of this signal is further modified by the electromagnetic coupling of the passive electrical resonant circuit of the sensor. This signal can be applied to a frequency discriminator that provides a signal from which the resonant frequency of the resonant circuit can be determined. In this aspect, the analog method can include generating a transmission signal using a tank circuit that includes a transmitting antenna; modifying the frequency of the transmission signal by electromagnetically coupling the passive electrical resonant circuit of the switched on sensor to the transmitting antenna; and converting the modified transmission signal into a standard signal for further application.

One exemplary method of interrogation is explained in more detail in commonly assigned U.S. patent application Ser. No. 11/105,294. In the described methodology, the interrogating system energizes the switched "on" sensor having the resonant circuit with a low duty cycle, gated burst of RF energy having a predetermined frequency or set of frequencies and a predetermined amplitude. The energizing signal is coupled to the passive electrical resonant circuit via a magnetic loop. The energizing signal induces a current in the passive electrical resonant circuit that is maximized when the frequency of the energizing signal is substantially the same as the resonant frequency of the passive electrical resonant circuit. The system receives the ring down response of the sensor via magnetic coupling and determines the resonant frequency of the sensor, which is then used to determine the measured characteristic acting on the respective sensor. In one aspect, the resonant frequency of the sensor is determined by adjusting the frequency of the energizing signal until the phase of the ring down signal and the phase of a reference signal are equal or at a constant offset. In this manner, the energizing signal frequency is locked to the sensor's resonant frequency and the resonant frequency of the sensor is known. The relative measured characteristic can then be ascertained.

In one aspect, the system can comprise a coupling loop that can be selectively positioned relative to the sensor to maximize the electromagnetic coupling between the passive electrical resonant circuit of the sensor and the coupling loop. The system can also provide the necessary isolation between the energizing signal and the output signal. In one aspect, it is contemplated that the system can energize the passive electrical resonant circuit of the sensor with a low duty cycle, gated burst of RF energy having a predetermined frequency or set of frequencies and a predetermined amplitude. The energizing signal can be electromagnetically coupled to the passive electrical resonant circuit of the sensor via one or more energizing loops. In operation, each energizing loop can be tuned to a different resonant frequency. The selection of the desired resonant frequencies can be based on the desired bandwidth, which, in one aspect of the invention and without limitation can range between about 30 to about 37.5 MHz.

The energizing signal induces a current in the passive electrical resonant circuit of the sensor that is maximized when the energizing frequency is the same as the resonant frequency of the passive electrical resonant circuit of the sensor. The system receives the ring down response of the sensor (or sensors) via one or more coupling loops and determines the resonant frequency of the sensor, which can be used to calculate the measured characteristic acting on the respective sensor.

In one aspect, a pair of phase locked loops ("PLLs") can be used to adjust the phase and the frequency of the energizing signal until its frequency locks to the resonant frequency of the passive electrical resonant circuit of the switched "on" sensor. In one embodiment, one PLL samples during the calibration cycle and the other PLL samples during the measurement cycle. In one non-limiting example, these cycles can alternate every 10 microseconds and can be synchronized with the pulse repetition period. In one aspect, the calibration cycle adjusts the phase of the energizing signal to a fixed reference phase to compensate for any system delay or varying environmental conditions. The environmental conditions that can affect the accuracy of the reading can include, but are not limited to, proximity of reflecting or magnetically absorbative objects, variation of reflecting objects located within transmission distance, variation of temperature or humidity which can change parameters of internal components, and aging of internal components.

In one aspect, one of the PLLs can be used to adjust the phase of the energizing signal and is referred to herein as the fast PLL. The other PLL can be used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator. The cycle in which the calibration signal is sampled is referred to as the calibration cycle. In one aspect, the system can adjust the phase of the energizing signal to drive the phase difference to zero or another select reference phase.

During the measurement cycle, the signal coupled from the passive electrical resonant circuit of the sensor (referred to herein as the output signal) can be processed and sampled to determine the phase difference between the output signal and the energizing signal. The system can then adjust the frequency of the energizing signal to drive the phase difference to zero or other reference phase. Once the slow PLL is locked, the frequency of the energizing signal is deemed to match the resonant frequency of the passive electrical resonant circuit of the sensor. The operation of the slow PLL is qualified based on signal strength so that the slow PLL does not lock unless the strength of the output signal meets a predetermined signal strength threshold.

In one aspect, a single un-tuned coupling loop can be is used. In this exemplary aspect, the loop can be connected to an input impedance that is high relative to the loop inductance. Optionally, multiple coupling loops can be used and each loop is tuned to a different resonant frequency.

In another aspect, the loops can be connected to a base unit 102 that generates the energizing signal and processes the output signal via a cable assembly. In this aspect, the cable assembly provides isolation between the energizing signal and the sensor signal by maximizing the distance between the coaxial cables that carry the signals and maintaining the relative positions of the coaxial cables throughout the cable assembly. In another exemplary aspect, the coaxial cables can be positioned on opposite sides of an internal cable, approximately 180 degrees apart. Shielding can also be used to isolate the energizing signal from the output signal. In one aspect, it is contemplated that additional shielding can be provided around each of the respective coaxial cables.

Figure 14:
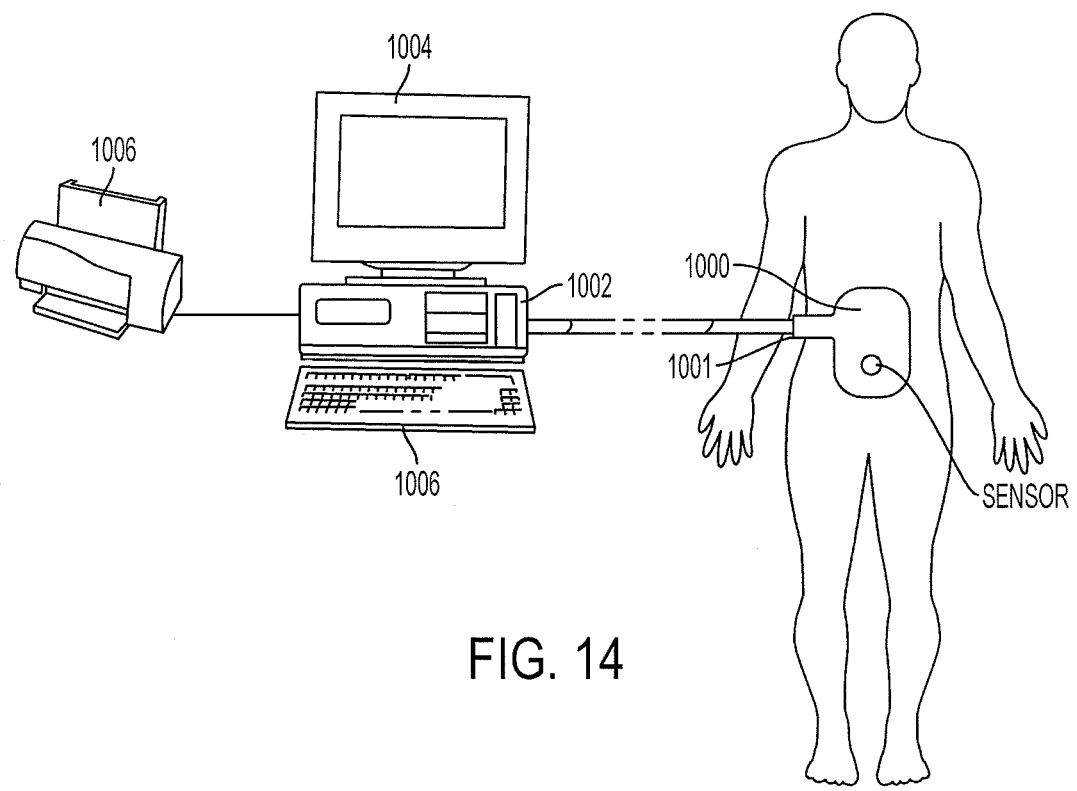
FIG. 14 illustrates an exemplary interrogation system for communicating with the at least one wireless pressure sensor that is positioned within a body.

In one aspect, FIG. 14 illustrates an exemplary interrogation system for communicating with the wireless apparatus described above that is positioned within a body. Without limitation, it is contemplated that the system can be used in at least two environments: the operating room during implant and the physician's office during follow-up examinations.

In one exemplary embodiment, the interrogation system can comprise a coupling loop 1000, the base unit 1002, a display device 1004, and an input device 1006, such as, for example and without limitation, a keyboard. In one exemplary embodiment, the base unit can include an RF amplifier, a receiver, and signal processing circuitry. In one aspect, the coupling loop 1000 can be configured to charge the passive electrical resonant circuit of the sensor and then couple signals from the energized passive electrical resonant circuit of the sensor into the receiver. Schematic details of the exemplary circuitry are illustrated in FIG. 14.

The display 1004 and the input device 1006 can be used in connection with the user interface for the system. In the embodiment illustrated in FIG. 14, the display device and the input device are conventionally connected to the base unit. In this embodiment, the base unit can also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface.

In one aspect, LABVIEW software can be used to provide the user interface, as well as to provide graphics, store and organize data and perform calculations for calibration and normalization. The user interface can record and display patient data and guide a user through surgical and follow-up procedures. In another aspect, an optional printer 1008 can be operably connected to the base unit and can be used to print out patient data or other types of information. As will be apparent to those skilled in the art in light of this disclosure, other configurations of the system, as well as additional or fewer components can be utilized with embodiments of the invention.

In one embodiment, the coupling loop can be formed from a band of copper. In this aspect, it is contemplated that the coupling loop comprises switching and filtering circuitry that is enclosed within a shielded box. The loop can be configured to charge the passive electrical resonant circuit of the sensor and then couple signals from the energized passive electrical resonant circuit of the sensor into a receiver. It is contemplated that the antenna can be shielded to attenuate in-band noise and electromagnetic emissions.

Figure 15:
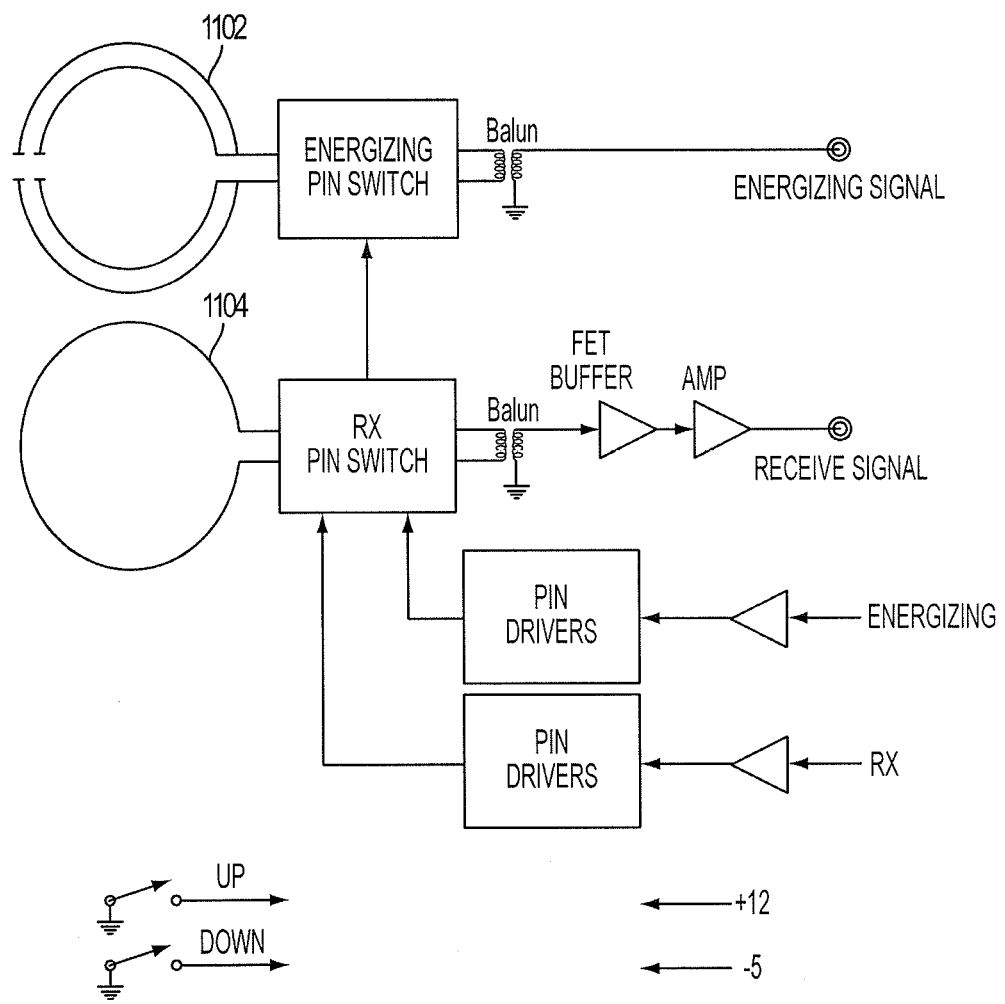
FIG. 15 is an exemplary block diagram of an exemplary coupling loop assembly for communication with at least one wireless pressure sensor.

In an alternative embodiment for a coupling loop, as shown in FIG. 15, separate loops for energizing 1102 and for receiving 1104 are provided, although a single loop can be used for both functions. PIN diode switching inside the loop sensor can be used to provide isolation between the energizing phase and the receive phase by opening the RX path pin diodes during the energizing period, and opening the energizing path pin diodes during the coupling period. It is contemplated in this embodiment that multiple energizing loops can be staggered tuned to achieve a wider bandwidth of matching between the transmit coils and the transmit circuitry.

In one aspect, the coupling loop or antenna can provide isolation between the energizing signal and the output signal, support sampling/reception of the output signal soon after the end of the energizing signal, and minimize switching transients that can result from switching between the energizing and the coupled mode. The coupling loop can also provide a relatively wide bandwidth, for example and without limitation, from between about 30 to about 37.5 MHz.

In one embodiment, separate loops can be used for transmitting the energizing signal to the passive electrical resonant circuit of the sensor and coupling the output signal from the energized passive electrical resonant circuit of the sensor. Two stagger-tuned loops can be used to transmit the energizing signal and an un-tuned loop with a high input impedance at the receiver can be used to receive the output signal. The term "coupling loop" is used herein to refer to both the loop(s) used to receive the output signal from the energized passive electrical resonant circuit of the sensor (the "sensor coupling loop"), as well as the loop sensor that includes the loop(s) used to transmit the energizing signal to the passive electrical resonant circuit of the sensor (the "energizing loop") and the sensor coupling loop(s).

During the measurement cycle, the sensor coupling loop can be configured to couple the output signal from the energized passive electrical resonant circuit of the sensor, which is relatively weak and dissipates quickly. In one aspect, the voltage provided to the receiver in the base unit depends upon the design of the sensor coupling loop and in particular, the resonant frequency of the loop.

In a further aspect, it is contemplated that the coupling loop can be un-tuned or tuned. FIG. 16A illustrates a loop that is un-tuned and FIG. 16B illustrates its equivalent circuit. The loop has an inductance, $L_1$, and is terminated into the receiver using a common input impedance, which can, for example and without limitation, be 50 ohms. The voltage at the receiver, $V_1$, is less than the open circuit voltage of the loop, i.e., the voltage that would be coupled by the loop if the loop was not terminated, $V_s$, and can be calculated as shown below.

$$V_1 = V_s \frac{50}{50 + j\omega L_1} \qquad \text{Equation 2}$$

Where L1 is the inductance of the loop and $\omega = 2\pi f$, with f=frequency in hertz.

To maximize the voltage at the receiver, it is contemplated that the loop can be tuned. FIG. 17A illustrates a loop that is tuned and FIG. 17B illustrates its equivalent circuit. In this aspect, the loop has an inductance, $L_1$, and a capacitance, $C_1$. The capacitance, $C_1$, is selected so that it cancels the inductance, $L_1$ at the resonant frequency, i.e., the series resonant circuit, $C_1$–$L_1$, is 0 ohms at the resonant frequency. At the resonant frequency the voltage at the receiver, $V_1$, equals the voltage coupled by the loop, $V_s$. One disadvantage of this type of loop is that it is optimized for a single frequency. If the loop is used in an environment where the frequency of the output signal is changing, then the capacitance is either changed dynamically or set to a compromise value (e.g., the loop is tuned to a single frequency within the band of interest).

To minimize this issue, another embodiment illustrated in FIGS. 18A and 18B uses an un-tuned loop with a high input impedance at the receiver. FIG. 18A illustrates a loop terminated into a receiver with a high input impedance and FIG. 18B illustrates its equivalent circuit. In this aspect, the input impedance at the receiver is selected so that the energy lost due to the loop impedance, $L_1$, is relatively insignificant. Using Zin as the input impedance at the receiver, the voltage at the receiver, $V_1$, is calculated as shown below.

$$V_1 = V_s \frac{Zin}{Zin + j\omega L_1} \qquad \text{Equation 3}$$

Since Zin is much larger than $j\omega L_1$, this can be approximated by the following equation $$V_1 = V_s \frac{\infty}{\infty + j\omega L_1}, \text{ or } V_1 = V_s \qquad \text{Equation 4}$$

As shown by the foregoing equation, the use of a relatively high input impedance at the input of the receiver negates $L_1$ for all frequencies. In one embodiment, a high impedance buffer can be inserted between the loop and an exemplary 50 ohm receiver circuit. In this embodiment, the high impedance buffer is on the order of 1 Mohm while the impedance of the loop is on the order of 200 ohms. In other embodiments, it is contemplated that the input impedance is at least two times the loop impedance.

Figure 19:
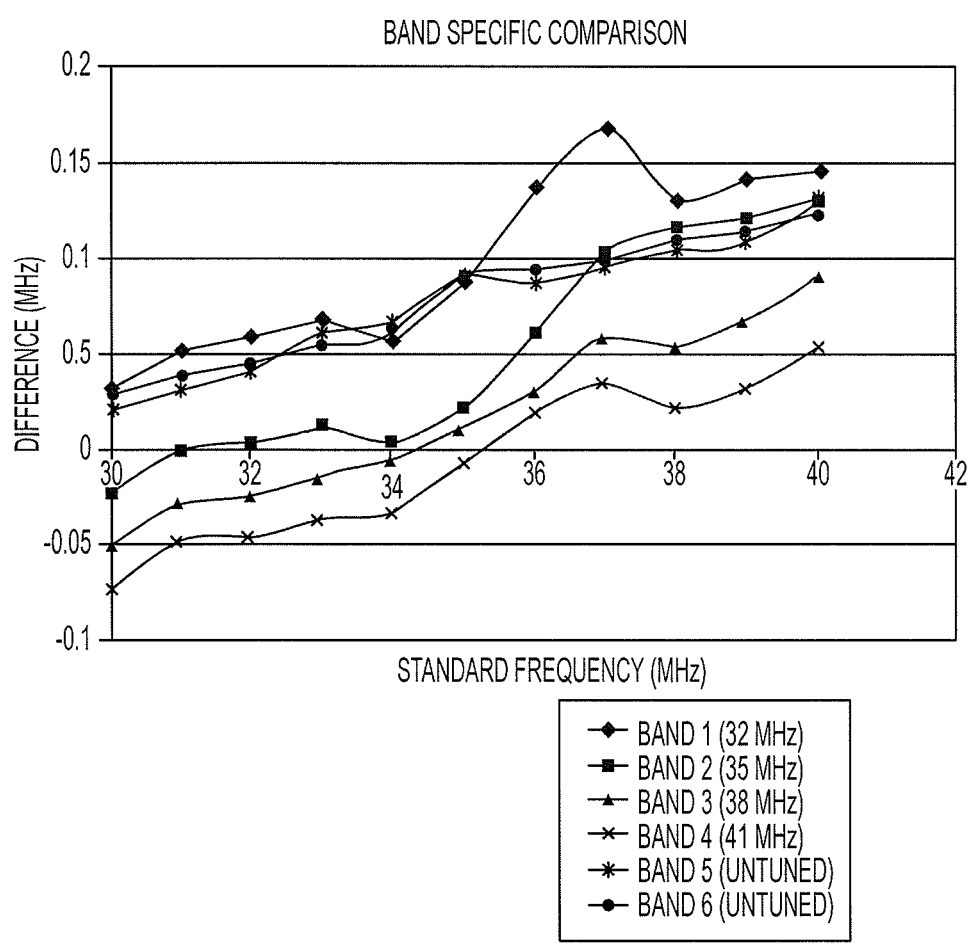
FIG. 19 is a graph that illustrates the comparison of the frequency response for tuned loops and the frequency response for un-tuned loops with high input impedances at the receiver.

In one aspect, the frequency response within the band of interest is more monotonic if the sensor coupling loop uses a high input impedance at the receiver, than if a tuned loop is used with a 50 ohm input impedance. FIG. 19 compares the frequency response for tuned loops and the frequency response for un-tuned loops with high input impedances at the receiver. The y-axis represents the difference in measured frequency between a calibration system using a network analyzer and the loop. The x-axis represents the frequency of the L-C standard used in the measurements. Linear interpolation can be used between measurement points. Band 1 corresponds to a loop resonant at 32 MHz, Band 2 corresponds to a loop resonant at 35 MHz, Band 3 corresponds to a loop resonant at 38 MHz, and Band 4 corresponds to a loop resonant at 41 MHz. Bands 1-4 correspond to a prior art design that uses switched capacitors banks to vary the loop resonance to achieve the needed bandwidth. Bands 5 and 6 correspond to un-tuned loops.

Bands 1-4 illustrate a slope variation within the band of interest, which can affect the accuracy of measurements made using the loop. Bands 5 and 6 illustrate that the variation within the band of interest is less than in the systems using a tuned loop. The more monotonic frequency response of an un-tuned loop with a high input impedance generally requires a simpler set of calibration coefficients to be used for the frequency conversion calculation.

An alternative embodiment to using an un-tuned loop and a high input impedance is to use stagger-tuned loops. If stagger tuned loops are used to receive the output signal, then the loops can be tuned in a manner similar to that described in the following paragraphs in connection with the transmission of an energizing signal.

During the energizing mode, the energizing loop produces a magnetic field. The intensity of the magnetic field produced by the energizing loop depends, in part, on the magnitude of the current within the loop. In one aspect, the current is maximized at the energizing frequency if the impedance of the loop is essentially 0 ohms at the energizing frequency. The resonant frequency of the loop is related to the loop inductance and capacitance, as shown below.

$$f_o = \frac{1}{2\pi\sqrt{L*C1}}$$ Equation 5

The impedance of the loop is preferably 0 ohms over the frequency range of interest, which, in an exemplary operating environment, can be, without limitation between about 30 MHz to about 37.5 MHz. To achieve the desired impedance over the desired frequency range, two or more loops can be stagger tuned as exemplarily shown in FIG. 20.

The resonant frequencies for the loops are based on the bandwidth of interest. If there are two loops, then the loops can be spaced geometrically. In one exemplary non-limiting aspect, the resonant frequency of the first loop is can be about 31 MHz and the resonant frequency of the second loop can be about 36.3 MHz, which corresponds to the pole locations of a second order Butterworth bandpass filter having about −3 dB points at about 30 MHz and about 37.5 MHz. Although FIG. 20 illustrates two loops, it is contemplated that other embodiments can use a different number of loops, which provides coverage for a much wider frequency range. In one aspect, the loops can be spaced logarithmically if there are more than two loops.

FIG. 21 illustrates the assembly of two stagger-tuned loops 1102, 1104 for transmitting the energizing signal to the passive electrical resonant circuit of the sensor and one un-tuned loop 1106 for receiving the output signal. In this aspect, the loops are parallel to one another with the un-tuned loop inside the stagger-tuned loops. Placing the loop used to receive the output signal inside of the loops used to transmit the energizing signal helps to shield the output signal from environmental interferences. In one embodiment, the loops can be positioned within a housing.

One will appreciate that the signal from an implanted passive sensor is relatively weak and is attenuated by the surrounding tissue and the distance between the sensor and the coupling loop. Optimizing the position and angle of the coupling loop relative to the sensor can help maximize the coupling between the sensor and the coupling loop. In one aspect, the coupling loop can be positioned so that a plane defined by the sensor coupling loop is approximately parallel to the inductor within the passive electrical resonant circuit of the sensor and the sensor is approximately centered within the sensor coupling loop.

In one aspect, isolation of the energizing signal and the output signal provided by the base unit and the coupling loop can be maintained in the cable that connects the base unit to the coupling loop. In one aspect, a cable can connect the base unit to the coupling loop and isolate the energizing signal, from the output signal. In one aspect, the distal end of the cable that connects to the base unit can comprise a multi-pin connector (e.g., AL06F15-ACS provided by Amphenol) and a right angle housing. The proximal end of the cable that connects to the coupling loop can comprise a first connector, which can be a multi-pin connector (e.g., AMP 1-87631-0 provided by Amphenol) that operably connects to the filtering and switching circuitry associated with the loop; a second connector that operably connects to the energizing loop; and a third connector that operably connects to the loop that couples the signal from the sensor. In this exemplary aspect, the right angle housing and the strain relief provide strain relief at the respective ends of the cable. When assembled with the housing, the strain relief can be positioned proximate to the housing. Optionally, other types of strain relief can be implemented, including, without limitation, physical constraints, such as tie wraps, ferrals or epoxy, and/or service loops. In one aspect, the cable can also comprise ferrite beads, which can help reduce ground currents within the cable.

In one aspect, the position of the coaxial cables within the cable is designed to maximize the isolation between the energizing signal and the sensor signal, while minimizing the diameter of the cable. The cable is configured to maximize the isolation between the coax cable that transmits the energizing signal and the inner bundle and the twisted pairs and the coax cable that receives the sensor signal and the inner bundle.

In an alternative embodiment and referring now to FIGS. 22(*a*)-29, the interrogation system can be configured to determine the resonant frequency of the sensor (and therefore the desired measured characteristic) by adjusting the phase and frequency of an energizing signal until the frequency of this signal locks to the resonant frequency of the sensor. In one aspect, the interrogation system energizes the switched "on" sensor with a low duty cycle, gated burst of RF energy of a predetermined frequency or set of frequencies and predetermined amplitude. This signal induces a current in the sensor that can be used to track the resonant frequency of the sensor. The interrogation system receives the ring down response of the sensor and determines the resonant frequency of the sensor, which is used to calculate the measured characteristic, such as, for example, pressure, acting thereon the sensor. As described above, interrogation the system can use a pair of PLL's to adjust the phase and the frequency of the energizing signal to track the resonant frequency of the sensor. In one exemplary aspect, the first measurement can be taken during introduction of the sensor for calibration and the second measurement can be taken after placement for functional verification of the sensor.

The interrogation system communicates with the implanted sensor to determine the resonant frequency of the sensor, which can comprise an LC resonant circuit having a variable capacitor. In one exemplary aspect, and not meant to be limiting, the distance between the plates of the variable capacitor varies as the surrounding pressure varies. Thus, the resonant frequency of the circuit can be used to determine the pressure acting thereon the sensor.

In one aspect, the interrogation system can energize the switched "on" sensor with an RF burst. The energizing signal can be a low duty cycle, gated burst of RF energy of a predetermined frequency or set of frequencies and predetermined amplitude. In one non-limiting example, the duty cycle of the energizing signal can range between about 0.1% to 50%. In another non-limiting example, the interrogation system can energize the sensor with a 30-37.5 MHz fundamental signal at a pulse repetition rate of 100 kHz with a duty cycle of 20%. The energizing signal is coupled to the sensor via a magnetic loop. This signal induces a current in the sensor which has maximum amplitude at the resonant frequency of the sensor. During this time, the sensor charges exponentially to a steady-state amplitude that is proportional to the coupling efficiency distance between the sensor and loop, and the RF power.

FIG. 27 shows the charging response of a typical LC circuit to a burst of RF energy at its resonant frequency. The speed at which the sensor charges is directly related to the Q (quality factor) of the sensor. Therefore, it is contemplated that the "on time" of the pulse repetition duty cycle can be optimized for the Q of the sensor. The system receives the ring down response of the sensor via magnetic coupling and determines the resonant frequency of the sensor.

FIG. 22A illustrates a typical energizing signal and FIGS. 22B, 22C and 22D illustrate typical coupled signals for various values of Q (quality factor) for the sensor. When the main unit is coupling energy at or near the resonant frequency of the sensor, the amplitude of the sensor return is maximized, and the phase of the sensor return will be close to zero degrees with respect to the energizing phase. The sensor return signal is processed via phase-locked-loops to steer the frequency and phase of the next energizing pulse.

In a further aspect, FIG. 23 illustrates a schematic diagram of the signal processing components within an exemplary base unit 1002. In one aspect, the base unit determines the resonant frequency of the sensor by adjusting the energizing signal so that the frequency of the energizing signal matches the resonant frequency of the sensor. In the exemplary embodiment illustrated by FIG. 23, two separate processors 1302, 1322 and two separate coupling loops 1340, 1342 are shown. In one embodiment, processor 1302 is associated with the base unit and processor 1322 is associated with a computer connected to the base unit. In other embodiments, it is contemplated that a single processor can be used to provide the same functions as the two separate processors. In other embodiments, it is also contemplated that a single loop can be used for both energizing and for coupling the sensor energy back to the receiver. As will be apparent to those skilled in the art, other configurations of the base unit are possible that use different components.

In one aspect, a pair of PLLs can be used. Is this aspect, the fast PPL is used to adjust the phase of the energizing signal and the slow PLL is used to adjust the frequency of the energizing signal. The base unit 1002 can be configured to provide two cycles: the calibration cycle and the measurement cycle. In one aspect, the first cycle is a 10 microsecond energizing period for calibration of the system, which is referred to herein as the calibration cycle, and the second cycle is a 10 microsecond energizing/coupling period for energizing the switched on sensor and coupling a return signal from the sensor, which is referred to herein as the measurement cycle.

During the calibration cycle, the interrogation system generates a calibration signal for system and environmental phase calibration and during the measurement cycle the system both sends and listens for a return signal, i.e. the sensor ring down. Alternatively, as those skilled in the art will appreciate, it is contemplated that the calibration cycle and the measurement cycle can be implemented in the same pulse repetition period.

The phase of the energizing signal is adjusted during the calibration cycle by the fast PLL and the frequency of the energizing signal is adjusted during the measurement cycle by the slow PLL. The following description of the operation of the PLLs is presented sequentially for simplicity. However, as those skilled in the art will appreciate, the PLLs can operate simultaneously.

Initially the frequency of the energizing signal is set to a default value determined by the calibration parameters of the sensor. Each sensor is associated with a number of calibration parameters, such as frequency, offset, and slope. An operator of the interrogation system enters the sensor calibration parameters into the interrogation system via the user interface and the interrogation system determines an initial frequency for the energizing signal based on the particular sensor. Alternatively, the sensor calibration information could be stored on portable storage devices, bar codes, or incorporated within a signal returned from the sensor. In one aspect, the initial phase of the energizing signal can be arbitrary.

The initial frequency and the initial phase are communicated from the processor 1302 to the DDSs (direct digital synthesizers) 1304, 1306. The output of DDS1 1304 is set to the initial frequency and initial phase and the output of DDS2 1306 (also referred to as local oscillator 1) is set to the initial frequency plus the frequency of the local oscillator 2. In one aspect, the phase of DDS2 is a fixed constant. In one embodiment, the frequency of local oscillator 2 is 4.725 MHz. The output of DDS1 is gated by the field programmable gate array (FPGA) 1308 to create a pulsed transmit signal having a pulse repetition frequency ("PRF"). The FPGA provides precise gating so that the base unit can sample the receive signal during specific intervals relative to the beginning or end of the calibration cycle.

During the calibration cycle, the calibration signal which enters the receiver 1310 is processed through the receive section 1311 and the IF section 1312, and is sampled. In one embodiment, the calibration signal is the portion of the energizing signal that leaks into the receiver (referred to herein as the energizing leakage signal). The signal is sampled during the on time of the energizing signal by a sample and hold circuit 1314 to determine the phase difference between the signal and local oscillator 2. FIG. 23 illustrates two cascaded sample and holds in circuit 1314 to provide both fast sampling and a long hold time. Alternatively, a single sample and hold can be used in circuit 1314. In the embodiment where the calibration signal is the portion of the energizing signal that leaks into the receiver, the signal is sampled approximately 100 ns after the beginning of the energizing signal pulse. Since the energizing signal is several orders of magnitude greater than the coupled signal, it is assumed that the phase information associated with the leaked signal is due to the energizing signal and the phase delay is due to the circuit elements in the coupling loop, circuit elements in the receiver, and environmental conditions, such as proximity of reflecting objects.

The phase difference is sent to a loop filter 1316. The loop filter is set for the dynamic response of the fast PLL. In one embodiment, the PLL bandwidth is 1000 Hz and the damping ratio is 0.7. A DC offset is added to allow for positive and negative changes. The processor 1302 reads its analog to digital converter (A/D) port to receive the phase difference information and adjusts the phase sent to direct digital synthesizer 1 (DDS1) to drive the phase difference to zero. This process is repeated alternatively until the phase difference is zero or another reference phase.

The phase adjustment made during the energizing period acts to zero the phase of the energizing signal with respect to local oscillator 2. Changes in the environment of the antenna or the receive chain impedance, as well as the phase delay within the circuitry prior to sampling affect the phase difference reading and are accommodated by the phase adjustment.

During the measurement cycle, the energizing signal may be blocked from the receiver during the on time of the energizing signal. During the off time of the energizing signal, the receiver is unblocked and the coupled signal from the sensor is received. The coupled signal is amplified and filtered through the receive section 1311. The signal is down converted and additional amplification and filtering takes place in the IF section 1312. In one embodiment, the signal is down converted to 4.725 MHz. After being processed through the IF section, the signal is mixed with local oscillator 2 and sampled by sample and hold circuits 1315 to determine the phase difference between the coupled signal and the energizing signal. FIG. 23 illustrates two cascaded sample and holds in circuit 1315 to provide both fast sampling and a long hold time. Alternatively, a single sample and hold can be used in circuit 1315. In one embodiment, the sampling occurs approximately 30 ns after the energizing signal is turned off.

In other aspects, group delay or signal amplitude can be used to determine the resonant frequency of the sensor. The phase curve of a second order system passes through zero at the resonant frequency. Since the group delay (i.e., the derivative of the phase curve) reaches a maximum at the resonant frequency, the group delay can be used to determine the resonant frequency. Alternatively, the amplitude of the sensor signal can be used to determine the resonant frequency. The sensor acts like a bandpass filter so that the sensor signal reaches a maximum at the resonant frequency.

The sampled signal is accumulated within a loop filter 1320. The loop filter is set for the dynamic response of the slow PLL to aid in the acquisition of a lock by the slow PLL. The PLLs are implemented with op-amp low pass filters that feed A/D inputs on microcontrollers, 1302 and 1322, which in turn talk to the DDSs, 1304 and 1306, which provide the energizing signal and local oscillator 1. The microcontroller that controls the energizing DDS 1304 also handles communication with the display. The response of the slow PLL depends upon whether the loop is locked or not. If the loop is unlocked, then the bandwidth is increased so that the loop will lock quickly. In one embodiment, the slow PLL has a damping ratio of 0.7 and a bandwidth of 120 Hz when locked (the Nyquist frequency of the blood pressure waveform), which is approximately ten times slower than the fast PLL.

A DC offset is also added to the signal to allow both a positive and a negative swing. The output of the loop filter is input to an A/D input of processor 1322. The processor determines a new frequency and sends the new frequency to the DSSs. The processor offsets the current frequency value of the energizing signal by an amount that is proportional to the amount needed to drive the output of the slow PLL loop filter to a preset value. In one embodiment the preset value is 2.5V and zero in phase. The proportional amount is determined by the PLL's overall transfer function.

The frequency of the energizing signal is deemed to match the resonant frequency of the sensor when the slow PLL is locked. Once the resonant frequency is determined, the measured characteristic can be calculated using the calibration parameters associated with the respective sensor, which results in a difference frequency that is proportional to the measured characteristic.

The operation of the slow PLL is qualified based on signal strength. The base unit includes signal strength detection circuitry. If the received signal does not meet a predetermined signal strength threshold, then the slow PLL is not allowed to lock and the bandwidth and search window for the PLL are expanded. Once the received signal meets the predetermined signal strength threshold, then the bandwidth and search window of the slow PLL is narrowed and the PLL can lock.

In one aspect, phase detection and signal strength determination can be provided via the "I" (in phase) and "Q" (quadrature) channels of a quadrature mixer circuit. The "I" channel is lowpass filtered and sampled to provide signal strength information to the processing circuitry. The "Q" channel is lowpass filtered and sampled (THSS, THSS2) to provide phase error information to the slow PLL.

The base unit can comprise two switches, RX blocking switches 1350 and 1352, that aid in the detection of the sensor signal. One of the RX blocking switches precedes the preselector in the receive section 1311 and the other RX blocking switch follows the mixer in the IF section 1312. The FPGA controls the timing of the RX blocking switches (control signals not shown). The RX blocking switches are closed during the on time of the energizing signal during the calibration cycle and generally closed during the off time of the energizing signal during the measurement cycle. During the measurement cycle the timing of the RX blocking switches is similar to the timing of the switch that controls the energizing signal into the receiver during the measurement cycle, but the RX blocking switches are closed slightly later to account for signal travel delays in the system. The RX blocking switches prevent the energizing signal that leaks into the receiver during the measurement cycle (specifically during the on time of the energizing signal) from entering the IF section. If the leakage signal enters the IF section, then it charges the IF section and the IF section may not settle out before the sensor signal arrives. For example, in one instance the IF section was charged for several hundred nanoseconds after the on time of the energizing signal. Blocking the leakage signal from the IF section eliminates this problem and improves detection of the sensor signal.

In another embodiment, the base unit can be configured to use multiple sampling points rather than the single sampling point discussed above in connection with FIG. 23. If a single sampling point is used and the sampling point coincides with a point where the average DC voltage of the phase detector is zero, then the system can lock even though the frequency is not the correct frequency. This situation can occur when there is system stress, such as a DC offset in the loop integrator or some other disturbance. The use of multiple sampling points helps prevent a false lock under these circumstances.

FIG. 28 illustrates a portion of the base unit for an embodiment that uses two sampling points, S1, S2. In this aspect, the components illustrated in FIG. 28 are used instead of the sample and hold components 1314, 1315 used in FIG. 23. As discussed above in connection with FIG. 23, this embodiment uses a pair of PLLs. The phase of the energizing signal is adjusted by the fast PLL and the frequency of the energizing signal is adjusted by the slow PLL. However, in this embodiment only a single cycle is needed to adjust the phase and frequency of the energizing signal, i.e. separate calibration and measurement cycles are not necessary. Since only a single cycle is used, the timing of the RX blocking switches is slightly different than that described above in connection with FIG. 23. In this embodiment, the RX blocking switches are generally closed during the off time of the energizing signal. The specific timing of the closure of the RX blocking switches may be system specific and can be adjusted to account for signal travel delays in the system.

The initial frequency and phase of the energizing signal are set as described above in connection with FIG. 23. The energizing signal may be blocked from the receiver during the on time of the energizing signal. During the off time of the energizing signal, the receiver is unblocked and the coupled signal from the sensor is received. The coupled signal is amplified and filtered through the receive section 1311. The signal is down converted and additional amplification and filtering takes place in the IF section 1312. In one aspect, the signal is down converted to 4.725 MHz. After being processed through the IF section, the signal is mixed with local oscillator 2 and sampled by the two sample and hold circuits 915a and 915b to determine the phase difference between the coupled signal and the energizing signal.

The two sample points are applied to a first differential amplifier 950 and a second differential amplifier 952. The first differential amplifier outputs a signal representing the difference between the two sampling points (S2−S1), which is fed into the loop filter 1320 and used to adjust the frequency of the energizing signal. The second differential amplifier 952 outputs a signal representing the sum of the two sampling points (S1+S2), which is fed into the loop filter 1316 and used to adjust the phase of the energizing signal.

In this aspect, the FPGA controls the timing of the two sample and hold circuits. In one aspect, the first sample point occurs approximately 30 ns after the energizing signal is turned off and the second sample point occurs approximately 100 to 150 ns after the energizing signal is turned off. The timing of the first sampling point can be selected so that the first sampling point occurs soon after the switching and filter transients have settled out. The timing of the second sampling point can be selected so that there is sufficient time between the first sampling point and the second sampling point to detect a slope, but before the signal becomes too noisy.

The frequency of the energizing signal is deemed to match the resonant frequency of the sensor when the slow PLL is locked. Once the resonant frequency is determined, the measured characteristic, such as pressure and the like, is calculated using the calibration parameters associated with the sensor, which results in a difference frequency that is proportional to the measured characteristic.

In yet another aspect, the base unit can use continuous signal processing techniques instead of the sampled processing techniques discussed above. This embodiment derives continuous wave signals from the pulsed calibration signal and the pulsed sensor signal and uses the continuous wave signals to adjust the phase and frequency of the energizing signal.

FIG. 29 illustrates a portion of the base unit for an embodiment that uses continuous signal processing. In this aspect, separate calibration 1212a and measurement sections 1212b can be used instead of the common IF section 1312 and separate sample and hold circuits 1314 and 1315 used in FIG. 23. In one aspect, after the signal passes through the receiver section 1311, the mixer, and one of the RX blocking switches, the signal is split into a pair of switches, TX IF switch 1250 and RX IF switch 1252. The FPGA controls the switches (control signals not shown) so that the TX IF switch 1250 is closed and the RX IF switch 1252 is opened during the calibration cycle and the TX IF switch is opened and the RX IF switch is closed during the measurement cycle. The calibration section 1212a and the measurement section 1212b can each include the aforementioned switch, a low pass filter, a narrow bandpass filter, amplifiers and a phase detector. The common IF section of FIG. 23 can use a bandpass filter, typically on the order of 2-3 MHz, whereas the calibration and measurements sections of FIG. 29 can use a narrow bandpass filter, typically on the order of 60-120 kHz.

In one aspect, it is contemplated that the system illustrated by FIG. 29 can use alternating calibration and measurement cycles. However, it is also contemplated that the calibration cycle and the measurement cycle can be implemented in the same pulse repetition period.

During the calibration cycle, the calibration signal which enters the receiver 1310 is processed through the receive section 1311 and the calibration section 1012a. The phase difference output from the calibration section is sent to the loop filter 1316 and the adjustment of the phase of the energizing signal proceeds as described above in connection with FIG. 23.

During the measurement cycle, the energizing signal can be blocked from the receiver during the on time of the energizing signal. During the off time of the energizing signal, the receiver is unblocked and the sensor signal is received. The coupled signal is amplified and filtered through the receive section 1311 and then transferred to the measurement section 1012b. The phase difference output from the measurement section is sent to loop filter 1320 and the adjustment of the frequency of the energizing signal proceeds as described above in connection with FIG. 23.

In one aspect, the RX blocking switches close as described above in connection with FIG. 23, but open earlier during the measurement cycle. Instead of being closed through the end of the off time of the energizing signal, the RX blocking switches open before the end of the off time. The timing of the opening of the RX blocking switches is based on the sensor characteristics and is selected so that the switches open once the sensor signal falls below the noise level. Since most of the energy from sensor signal is received within a time period of Q/fo, where Q is the Q of the sensor and fo is the center frequency of the sensor, the RX blocking switches can be opened after approximately Q/fo. For example, if the Q of the sensor if 40 and the fo is 32 MHz, then the RX blocking switches are opened after approximately 1.25 microseconds during the measurement cycle. The Q of the sensor and an approximate fo of the sensor are typically known and can be used to control the timing of the RX blocking switches.

In another aspect, the sampled information is used when utilizing the sample and hold techniques and the noise after the sample point(s) is ignored. However, in this continuous signal embodiment, all of the noise is seen unless other adjustments are made. Opening the RX blocking switches once the sensor signal decays below the noise level helps reduce the noise seen by the rest of the system and improves detection of the sensor signal.

The frequency spectrum of the sensor signal includes a number of spectral components that correspond to the pulse repetition frequency, including a strong component corresponding to the center frequency of the energizing signal (fo). The information needed to determine the resonant frequency of the sensor can be obtained by examining the phase of the spectral component that corresponds to fo. The measurement section isolates the spectral component at fo and the resulting time domain signal is a continuous wave signal.

In various aspects, the interrogation system generates an energizing signal with a random or pseudo random frame width. For example, the pulse width can be 2 microseconds for each frame, but the frame size can be pseudo randomly selected from a plurality of possible frame sizes, such as, for example and without limitation, 6.22 microseconds, 8.76 microseconds, 11.30 microseconds and 13.84 microseconds. It is contemplated that any number of frame sizes can be used, although at some point increasing the number of possible frame sizes can increase the interrogation system complexity with only incremental improvements.

In one aspect, the minimum frame sizes generally correspond to the smallest frame size that provides a sufficient receive window and typically corresponds to the pulse width. For example, and without limitation, if the pulse width is 2 microseconds, then the minimum receive window is also about 2 microseconds, which makes the minimum frame size about 4 microseconds. However, switching times and other practical considerations related to the components used may result in a slightly larger frame size. The maximum frame size is typically based on a desired average pulse repetition rate. In this example, if the average pulse repetition rate is selected as 10 microseconds, then the maximum frame size is about 14 microseconds.

If a random or pseudo random frame width is used, then the frame width can vary between the calibration cycle and the measurement cycle or a common frame width can be used for a calibration cycle and the following measurement cycle. The use of a random or pseudo random frame width helps isolate the spectral component needed to determine the resonant frequency of the sensor and relaxes the requirements of the narrow bandpass filter used in the receive section.

Optionally, the RX blocking switch 1352 can be combined with the TX IF switch 1050 and the RX IF switch 1052 and the control of the TX IF and the RX IF switches can be modified to accommodate the combination.

In another aspect, the interrogation system can be configured to minimize potential false lock problems. Typically, a false lock occurs if the interrogation system locks on a frequency that does not correspond to the resonant frequency of the sensor. In one aspect, a false lock can arise due to the pulsed nature of the system. Since the energizing signal is a pulsed signal, it includes groups of frequencies. The frequency that corresponds to a false lock is influenced by the pulse repetition frequency, the Q of the sensor, and the duty cycle of the RF burst. For example, a constant pulse repetition frequency adds spectral components to the return signal at harmonic intervals around the resonant frequency of the sensor, which can cause a false lock. In one embodiment, false locks occur at approximately 600 kHz above and below the resonant frequency of the sensor. To determine a false lock, the characteristics of the signal are examined. For example, pulse repetition frequency dithering and/or observing the slope of the baseband signal are two possible ways of determine a false lock. In one aspect where the system locks on a sideband frequency, the signal characteristics can correspond to a heartbeat or a blood pressure waveform, for example.

In another aspect, a false lock can arise due to a reflection or resonance of another object in the vicinity of the system. This type of false lock can be difficult to discern because it generally does not correspond to a heartbeat or blood pressure waveform for example. The lack of frequency modulation can be used to discriminate against this type of false lock. Changing the orientation of the magnetic loop can also affect this type of false lock because the reflected false lock is sensitive to the angle of incidence.

In yet another aspect, a false lock can arise due to switching transients caused by switching the PIN diodes and analog switches in the RF path. These transients cause damped resonances in the filters in the receive chain, which can appear similar to the sensor signal. For example, these types of false locks do not typically correspond to a heartbeat or blood pressure waveform because they are constant frequency. These types of false locks are also insensitive to orientation of the magnetic loop.

In one exemplary aspect, the interrogation system can be configured to prevent the occurrence of a false lock resulting from interrogation system locking on a frequency that does not correspond to the resonant frequency of the sensor. In this aspect, to avoid the false lock, the interrogation system determines the slope of the baseband signal (the phase difference signal at point 330). In one aspect, if the slope is positive, then the lock is deemed a true lock. However, if the slope is negative, then the lock is deemed a false lock. In another embodiment, a negative slope is deemed a true lock and a positive slope is deemed a false lock. The slope is determined by looking at points before and after the phase difference signal goes to zero. The slope can be determined in a number of different ways, including but not limited to, using an analog differentiator or multiple sampling. FIGS. 24A and 24B illustrate a true lock and a false lock respectively, when a positive slope indicates a true lock.

In another aspect, if a false lock is detected, then the signal strength can be suppressed so that the signal strength appears to the processor to be below the threshold and the system continues to search for the center frequency. In other aspect, any non-zero slope can be interpreted as a false lock resulting in zero signal strength.

In one aspect, the interrogation system can also use frequency dithering to avoid the occurrence of a false lock resulting from interrogation system locking on a frequency that does not correspond to the resonant frequency of the sensor. In this aspect, since the spectral components associated with a constant pulse repetition frequency can cause a false lock, dithering the pulse repetition frequency helps avoid a false lock. By dithering the pulse repetition frequency, the spectral energy at the potential false lock frequencies is reduced over the averaged sampling interval. As shown in FIG. 25, the energizing signal includes an on time t1 and an off time t2. The system can vary the on time or the off time to vary the PRF (PRF=1/(t1+t2)). FIG. 25 illustrates different on times (t1, t1') and different off times (t2, t2'). By varying the PRF, the sidebands move back and forth and the average of the sidebands is reduced. Thus, the system locks on the center frequency rather than the sidebands. The PRF can be varied between predetermined sequences of PRFs or can be varied randomly.

In another aspect, the coupling loop can switch between an energizing mode and a coupling mode. This switching can create transient signals, which can cause a false lock to occur. In one aspect, phase dithering is one method that can be used to reduce the switching transients. As shown in FIG. 26, the system receives a switching transient 1603 between the end of the energizing signal 1602 and the beginning of the coupled signal 1604. To minimize the transient, the phase of the energizing signal may be randomly changed. However, changing the phase of the energizing signal requires that the system redefine zero phase for the interrogation system. To redefine zero phase for the interrogation system, the phase of DDS2 is changed to match the change in phase of the energizing signal. Thus, the phase of the energizing signal 1602' and the coupled signal 1604' are changed, but the phase of the transient signal 1603' is not. As the system changes phase, the average of the transient signal is reduced.

Optionally, changing the resonant frequency of the antenna as it is switched from energizing mode to coupling mode also helps to eliminate the switching transients. The coupled signal appears very quickly after the on period of the energizing signal and dissipates very quickly. In one embodiment, the invention operates in a low power environment with a passive sensor so that the magnitude of the coupled signal is small. In one exemplary aspect, the coupling loop can be tuned to a resonant frequency that is based upon the sensor parameters. Changing the capacitors or capacitor network that is connected to the coupling loop changes the resonant frequency of the antenna. In one aspect, the resonant frequency can be changed from approximately 1/10% to 2% between energizing mode and coupled mode. Additionally, in some aspect, the coupling loop is untuned.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A wireless sensor, comprising:
   a primary passive electrical resonant circuit that is configured to be selectively electromagnetically coupled to an ex-vivo source of RF energy and that comprises a first inductor and a first capacitor;
   a secondary passive electrical resonant circuit further comprising a second inductor and a second capacitor, wherein the secondary passive electrical resonant circuit is responsive to the electromagnetic coupling of a predetermined frequency produced by the ex-vivo source of RF energy; and
   a switch operatively coupled to the primary passive electrical resonant circuit and the secondary passive electrical resonant circuit, wherein the switch is selectable between an off position, in which the primary passive electrical resonant circuit is de-tuned, and an on position, in which the primary passive electrical resonant circuit is tuned;
   wherein, when the switch is positioned in the on position, the primary passive electrical resonant circuit has an intrinsic electrical property that is variable in response to a characteristic of a patient, and wherein the primary passive electrical resonant circuit, in response to an energizing signal produced by the ex-vivo source of RF energy, is configured to generate a sensor signal characterized by a resonant frequency that is indicative of the characteristic.

2. The wireless sensor of claim 1, wherein at least one of the first inductor and first capacitor are variable in response to the characteristic of the patient.

3. The wireless sensor of claim 1, wherein the resonant frequency is dependent upon urged movement of a portion of the primary passive electrical resonant circuit and is indicative of the pressure applied thereon a portion of the respective sensor.

4. The wireless sensor of claim 1, wherein the characteristic is selected from a group consisting of: pressure, and temperature.

5. The wireless sensor of claim 1, further comprising means for selectively actuating the switch in response to the actuation of the secondary passive electrical resonant circuit.

6. The wireless sensor of claim 5, wherein the means for selectively actuating the switch comprises a storage capacitor that is configured to actuate the switch upon the accumulation of a predetermined voltage from the first passive electrical resonant circuit.

7. The wireless sensor of claim 1, wherein the switch remains in the on position for a predetermined period of time.

8. The wireless sensor of claim 7, wherein the predetermined period of time is a RC time constant, wherein the storage capacitor is electrically coupled to a storage resistor, and wherein the RC time constant is a function of the storage capacitor and the storage resistor.

9. The wireless sensor of claim 1, wherein the switch is binary.

10. The wireless sensor of claim 1, wherein the on position is a default position.

11. The wireless sensor of claim 10, wherein the switch comprises an N-type MOSFET switch.

12. The wireless sensor of claim 1, wherein the off position is a default position.

13. The wireless sensor of claim 12, wherein the switch comprises a P-type MOSFET switch.

14. The wireless sensor of claim 1, wherein the switch is selected from a group consisting of: an N-type MOSFET switch and a P-type MOSFET switch.

15. The wireless sensor of claim 1, wherein the predetermined frequency is a substantially monochromatic frequency.

16. The wireless sensor of claim 1, further comprising an ex-vivo processor programmed to perform the steps of:
   generating the energizing signal;
   receiving the sensor signal;
   sampling the sensor signal using at least two sample points;
   based on the at least two sample points, adjusting a frequency and a phase of the energizing signal; and
   using the frequency of the energizing signal to determine the resonant frequency.

17. The wireless sensor of claim 16, wherein the processor is further programmed to perform the step of using the at least two sample points of the sensor signal to determine whether a phase slope exists.

18. The wireless sensor of claim 16, wherein the processor is further programmed to perform the step of determining a sum of the sample points, wherein adjusting a frequency and a phase of the energizing signal comprises using the sum to adjust the phase of the energizing signal.

19. The wireless sensor of claim 16, wherein the processor is further programmed to perform the step of determining a difference of the sample points, wherein adjusting a frequency and a phase of the energizing signal comprises using the difference to adjust the frequency of the energizing signal.

20. The wireless sensor of claim 1, further comprising an ex-vivo processor programmed to perform the steps of:
   adjusting a frequency of the energizing signal by:
      receiving the sensor signal from the wireless sensor during a measurement cycle;
      processing the sensor signal during a period within the measurement cycle to create a continuous wave IF sensor signal;
      determining a phase difference between the IF sensor signal and the energizing signal;
      based on the phase difference adjusting the frequency of the energizing signal to reduce the phase difference; and
      determining the frequency of the energizing signal when the phase difference corresponds to a predetermined value; and
   using the frequency of the energizing signal when the phase difference corresponds to the predetermined value to determine the resonant frequency.

21. The wireless sensor of claim 20, wherein the processor is further programmed to perform the steps of:
   adjusting a phase of the energizing signal by:
      generating the energizing signal;
      receiving a calibration signal during a calibration cycle;
      processing the calibration signal during a first period within the calibration cycle to create a continuous wave IF calibration signal;
      determining a first phase difference between the IF calibration signal and a reference signal; and
      adjusting the phase of the energizing signal to reduce the first phase difference based on the first phase difference.

22. The wireless sensor of claim 21, wherein generating the energizing signal comprises adjusting a frame width of the energizing signal between a first cycle and a second cycle.

23. The wireless sensor of claim 21, wherein processing the calibration signal during a first period within the calibration cycle comprises allowing the calibration signal to propagate into a calibration section during the first period.

24. The wireless sensor of claim 21, further comprising preventing the calibration signal from propagating into a measurement section during the calibration cycle.

25. The wireless sensor of claim 21, wherein adjusting the phase of the energizing signal comprises using a first phase locked loop and adjusting the frequency of the energizing signal comprises using a second phase locked loop.

26. The wireless sensor of claim 1, further comprising an ex-vivo processor programmed to perform the steps of:
   providing a calibration cycle, wherein the calibration cycle includes: generating the energizing signal;
      receiving a calibration signal; and
      comparing the energizing signal and the calibration signal to determine a phase difference; and
   providing a measurement cycle, wherein the measurement cycle includes:
      energizing the wireless sensor;
      receiving the sensor signal from the wireless sensor;
      comparing the sensor signal and a reference signal to determine a second phase difference; and
      using the second phase difference to determine the resonant frequency.

27. The wireless sensor of claim 26, wherein the calibration cycle further comprises adjusting a phase of the energizing signal until the phase difference is a predetermined value, and wherein the measurement cycle further comprises adjusting a frequency of the energizing signal to reduce the second phase difference.

28. The wireless sensor of claim 26, wherein using the second phase difference to determine the frequency of the wireless sensor comprises using the frequency of the energizing signal to determine the resonant frequency of the wireless sensor.

29. The wireless sensor of claim 26, wherein the measurement cycle is repeated until the second phase difference is a predetermined value, and wherein the calibration cycle is repeated until the second phase difference is a predetermined value.

30. A wireless sensor, comprising:
   a primary passive electrical resonant circuit that is configured to be selectively electromagnetically coupled to an ex-vivo source of RF energy and that comprises a first inductor and a first capacitor;
   a secondary passive electrical resonant circuit further comprising a second inductor and a second capacitor, wherein the secondary passive electrical resonant circuit is responsive to the electromagnetic coupling of a predetermined frequency produced by the ex-vivo source of RF energy; and
   a means for selectively positioning the primary passive resonant circuit in a tuned position in response to the actuation of the secondary passive electrical resonant circuit;
   wherein, in the tuned position, the primary passive electrical resonant circuit has an intrinsic electrical property that is variable in response to a characteristic of a patient, and wherein the primary passive electrical resonant circuit, in response to an energizing signal produced by the ex-vivo source of RF energy, is configured to generate a sensor signal characterized by a resonant frequency that is indicative of the characteristic.

31. The wireless sensor of claim 30, wherein the means for selectively positioning the primary passive resonant circuit comprises a switch operatively coupled to the primary passive electrical resonant circuit and the secondary passive electrical resonant circuit, wherein the switch is selectable between an off position, in which the primary passive electrical resonant circuit is de-tuned, and an on position, in which the primary passive electrical resonant circuit is tuned.

32. The wireless sensor of claim 31, wherein the means for selectively positioning the primary passive resonant circuit further comprising means for selectively actuating the switch in response to the actuation of the secondary passive electrical resonant circuit.

33. The wireless sensor of claim 32, wherein the means for selectively actuating the switch comprises a storage capacitor that is configured to actuate the switch upon the accumulation of a predetermined voltage from the first passive electrical resonant circuit.

34. The wireless sensor of claim 33, wherein the switch remains in the on position for a predetermined period of time.

35. The wireless sensor of claim 34, wherein the predetermined period of time is a RC time constant, wherein the storage capacitor is electrically coupled to a storage resistor, and wherein the RC time constant is a function of the storage capacitor and the storage resistor.

36. A wireless sensor, comprising:
   a primary passive electrical resonant circuit comprising of a first passive electrical resonant circuit configured to measure a first characteristic of a patient and a second passive electrical resonant circuit configured to measure a second characteristic of the patient, wherein each respective first and second passive electrical circuit is configured to be selectively electromagnetically coupled to an ex-vivo source of RF energy and comprises a first inductor and a first capacitor;

a secondary passive electrical resonant circuit further comprising a second inductor and a second capacitor, wherein the secondary passive electrical resonant circuit is responsive to the electromagnetic coupling a predetermined frequency produced by the ex-vivo source of RF energy; and a means for selectively tuning one of the respective first and second passive electrical circuits in response to the actuation of the secondary passive electrical resonant circuit;

wherein, in the tuned position, the first passive electrical resonant circuit has an intrinsic electrical property that is variable in response to the first characteristic of the patient, wherein the first passive electrical resonant circuit, in response to a first energizing signal produced by the ex-vivo source of RF energy, is configured to generate an first sensor signal characterized by a first resonant frequency that is indicative of the first characteristic, wherein, in the tuned position, the second passive electrical resonant circuit has an intrinsic electrical property that is variable in response to the second characteristic of the patient, and wherein the second passive electrical resonant circuit, in response to a second energizing signal produced by the ex-vivo source of RF energy, is configured to generate a second sensor signal characterized by a second resonant frequency that is indicative of the second characteristic.

37. The wireless sensor of claim 36, wherein the means for selectively tuning one of the respective first and second passive electrical circuits comprises a switch operatively coupled to the primary passive electrical resonant circuit and the secondary passive electrical resonant circuit, wherein the switch is selectable between a first position, in which the first passive electrical resonant circuit is tuned, and a second position, in which the second passive electrical resonant circuit is tuned.

38. The wireless sensor of claim 37, wherein the means for selectively positioning the primary passive resonant circuit further comprising means for selectively actuating the switch in response to the actuation of the secondary passive electrical resonant circuit.

39. The wireless sensor of claim 38, wherein the means for selectively actuating the switch comprises a storage capacitor that is configured to actuate the switch upon the accumulation of a predetermined voltage from the first passive electrical resonant circuit.

40. The wireless sensor of claim 39, wherein the switch remains in the first position for a predetermined period of time.

41. The wireless sensor of claim 40, wherein the predetermined period of time is a RC time constant, wherein the storage capacitor is electrically coupled to a storage resistor, and wherein the RC time constant is a function of the storage capacitor and the storage resistor.

42. The wireless sensor of claim 36, wherein the first energizing signal and the second energizing signal are substantially identical.

\* \* \* \* \*